(12) United States Patent
Rao et al.

(10) Patent No.: US 11,820,809 B2
(45) Date of Patent: Nov. 21, 2023

(54) MULTISPECIFIC ANTIBODIES FACILITATING SELECTIVE LIGHT CHAIN PAIRING

(71) Applicant: SANOFI, Paris (FR)

(72) Inventors: Ercole Rao, Frankfurt am Main (DE); Christian Beil, Frankfurt am Main (DE); Christian Lange, Frankfurt am Main (DE); Katja Kroll, Frankfurt am Main (DE); Wulf-Dirk Leuschner, Frankfurt am Main (DE); Ingo Focken, Frankfurt am Main (DE); Thomas Langer, Frankfurt am Main (DE); Nadja Spindler, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/687,055

(22) Filed: Aug. 25, 2017

(65) Prior Publication Data

US 2018/0057567 A1    Mar. 1, 2018

(30) Foreign Application Priority Data

Aug. 26, 2016  (EP) ...................................  16306087

(51) Int. Cl.
| | |
|---|---|
| C07K 16/00 | (2006.01) |
| C07K 16/46 | (2006.01) |
| C07K 16/24 | (2006.01) |
| C07K 16/28 | (2006.01) |

(52) U.S. Cl.
CPC ............ *C07K 16/00* (2013.01); *C07K 16/244* (2013.01); *C07K 16/247* (2013.01); *C07K 16/2809* (2013.01); *C07K 16/2866* (2013.01); *C07K 16/468* (2013.01); *C07K 2317/31* (2013.01); *C07K 2317/35* (2013.01); *C07K 2317/41* (2013.01); *C07K 2317/50* (2013.01); *C07K 2317/515* (2013.01); *C07K 2317/52* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2317/622* (2013.01); *C07K 2317/64* (2013.01); *C07K 2317/66* (2013.01); *C07K 2317/76* (2013.01); *C07K 2317/92* (2013.01)

(58) Field of Classification Search
CPC .............. C07K 16/468; C07K 2317/31; C07K 2317/60; C07K 2317/66; C07K 2317/64
USPC ........................................... 424/133.1, 136.1
See application file for complete search history.

(56) References Cited

U.S. PATENT DOCUMENTS

| | | | | |
|---|---|---|---|---|
| 9,163,079 | B2* | 10/2015 | Poppe | C07K 16/00 |
| 2010/0226923 | A1 | 9/2010 | Rao et al. | |
| 2010/0316641 | A1* | 12/2010 | Dimitrov | C07K 16/005 424/133.1 |
| 2012/0276099 | A1* | 11/2012 | Poppe | C07K 16/00 424/134.1 |
| 2014/0023645 | A1* | 1/2014 | Dimitrov | C07K 16/005 424/133.1 |
| 2016/0046703 | A1* | 2/2016 | Poppe | C07K 16/00 424/93.7 |
| 2017/0081393 | A1* | 3/2017 | Dimitrov | C07K 16/005 |
| 2018/0194861 | A1* | 7/2018 | Dong | C07K 16/468 |
| 2019/0048098 | A1* | 2/2019 | Preyer | A61K 39/395 |
| 2019/0144565 | A1* | 5/2019 | Adams | A61P 37/08 424/140.1 |

FOREIGN PATENT DOCUMENTS

| | | |
|---|---|---|
| EP | 2210902 | 7/2010 |
| JP | 2015-514997 A | 10/2013 |
| JP | 2015-514405 A | 5/2015 |
| JP | 2015-180226 A | 10/2015 |
| WO | 2011/090762 A1 | 7/2011 |
| WO | 2011/097603 A1 | 8/2011 |
| WO | 2012/135345 A1 | 10/2012 |
| WO | 2013/156054 A1 | 10/2013 |
| WO | 2013/156148 A1 | 10/2013 |
| WO | 2013/159117 A1 | 10/2013 |
| WO | 2017011342 A1 | 1/2017 |

OTHER PUBLICATIONS

Seifert et al. (Protein Engineering, Design & Selection vol. 25 No. 10 pp. 603-612, 2012; published online Sep. 17, 2012).*
Worn and Pluckthun (J. Mol. Biol. Feb. 2, 2001;305(5):989-1010).*
Vajda et al., "Progress toward improved understanding of antibody maturation," Current Opinion in Structural Biology, 67 pp. 226-231 (2021)).*
Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Altschul et al., "Basic local alignment search tool," J. Mol. Biol. 1990, 215(3): 403-10.
Altschul et al., "Gapped BLAST and PSI-BLAST: a new generation of protein database search programs," Nucleic Acids Res. 1997, 25(17): 3389-402.

(Continued)

*Primary Examiner* — Lynn A Bristol
(74) *Attorney, Agent, or Firm* — McDonnell Boehnen Hulbert & Berghoff LLP

(57) ABSTRACT

Provided herein are multispecific antibodies, e.g. bispecific antibodies, which are modified such that the desired chain pairing takes place and/or can be selected for. Specifically, this is achieved by using different dimerization domains for light chain pairing. Also disclosed herein are nucleic acids encoding for these antibodies, expression vectors comprising these nucleic acids, cells expressing them, and further to pharmaceutical compositions comprising the antibodies, as well as methods of isolating the antibodies.

14 Claims, 12 Drawing Sheets

Specification includes a Sequence Listing.

(56) References Cited

OTHER PUBLICATIONS

Atwell S. et al., "Stable heterodimers from remodeling the domain interface of a homodimer using a phage display library," J. Mol. Biol. 1997, 270(1): 26-35.
Extended European Search Report, Nov. 25, 2016, Issued for European Application No. 16306087.4.
Hezareh et al., "Effector function activities of a panel of mutants of a broadly neutralizing antibody against human immunodeficiency virus type 1," J. Virol. 2001, 75(24): 12161-68.
Jackman et al., "Development of a two-part strategy to identify a therapeutic human bispecific antibody that inhibits IgE receptor signaling," J. Biol. Chem. 2010, 285(27): 20850-59.
Karlin and Altschul, "Applications and statistics for multiple high-scoring segments in molecular sequences," Proc. Natl. Acad. Sci. USA 1993, 90(12): 5873-77.
Klein et al., "Progress in overcoming the chain association issue in bispecific heterodimeric IgG antibodies," MABS, Nov. 2012 653-63 (Nov. 2012).
Merchant et al., "An efficient route to human bispecific IgG," Nat. Biotechnol. 1998, 16(7): 677-81.
Murphy et al., "Structural variation in immunoglobulin constant regions," Janeway's Immunobiology, Jan. 2008, 160-67.
Ridgway et al., "'Knobs-into-holes' engineering of antibody CH3 domains for heavy chain heterodimerization," Protein Eng. 1996, 9(7): 617-21.
Spiess et al., "Alternative molecule formats and therapeutic applications for bispecific antibodies," Molecular Immunology, 67 (2 Pt. A.) Jan. 2015, 95-106.
Starez et al., "Hybrid antibodies can target sites for attack by T cells," Nature, 1985, 314(6012): 628-31.
Suresh et al., "Advantages of bispecific hybridomas in one-step immunocytochemistry and immunoassays," Proc. Natl. Acad. Sci. U.S.A. 1986, 83(20): 7989-93.
UniProt No. P01854, Jul. 1986, pp. 1-8; see p. 6.
UniProt No. P01871, Jul. 2008-v3, pp. 1-13; see p. 13.
Seifert et al. "Tetravalent Antibody-scTRAIL Fusion Proteins with Improved Properties." Mol. Cancer Ther 2013, 13(1): 101-111.
Pelsue S., Fundamentals of Antibody Structure & Function. Marine Biotechnology.

* cited by examiner

A

B

C

D

D

E

MULTISPECIFIC ANTIBODIES FACILITATING SELECTIVE LIGHT CHAIN PAIRING

This application claims the benefit of European Application No. 16 306807.4, filed Aug. 26, 2016, the disclosure of which is herein incorporated by reference in its entirety.

DESCRIPTION

Provided herein are multispecific antibodies, e.g. bispecific antibodies, which are modified such that the desired chain pairing takes place and/or can be selected for. Specifically, this is achieved by using different dimerization domains for light chain pairing. Also disclosed herein are nucleic acids encoding for these antibodies, expression vectors comprising these nucleic acids, cells expressing them, and further to pharmaceutical compositions comprising the antibodies, as well as methods of isolating the antibodies.

Naturally occurring IgG antibodies are bivalent and monospecific. Multispecific, e.g. bispecific antibodies having binding specificities for multiple different antigens can be produced using recombinant technologies and are projected to have broad clinical applications. It is well known that complete IgG antibody molecules are Y-shaped molecules comprising four polypeptide chains: two heavy chains and two light chains. Each light chain consists of two domains, the N-terminal domain being known as the variable or $V_L$ domain (or region) and the C-terminal domain being known as the constant (or $C_L$) domain (constant kappa ($C_K$) or constant lambda ($C_\lambda$) domain). Each heavy chain consists of four or five domains, depending on the class of the antibody. The N-terminal domain is known as the variable (or $V_H$) domain (or region), which is followed by the first constant (or $C_H1$) domain, the hinge region, and then the second and third constant (or $C_H2$ and $C_H3$) domains. In an assembled antibody, the VL and $V_H$ domains associate together to form an antigen binding site. Also, the $C_L$ and $C_H1$ domains associate together to keep one heavy chain associated with one light chain. The two heavy-light chain heterodimers associate together by interaction of the $C_H2$ and $C_H3$ domains and interaction between the hinge regions on the two heavy chains.

It has been of interest to produce multispecific antibodies, e.g. bispecific antibodies (BsAbs) that combine the antigen binding sites of several antibodies within a single molecule, and therefore, would be able to bind several different antigens simultaneously. Besides applications for diagnostic purposes, such molecules pave the way for new therapeutic applications, e.g., by redirecting potent effector systems to diseased areas (where cancerous cells often develop mechanisms to suppress normal immune responses triggered by monoclonal antibodies, like antibody-dependent cellular cytotoxicity (ADCC) or complement-dependent cytotoxicity (CDC)), or by increasing neutralizing or stimulating activities of antibodies. This potential was recognized early on, leading to a number of approaches for obtaining such multispecific antibodies. Initial attempts to couple the binding specificities of two whole antibodies against different target antigens for therapeutic purposes utilized chemically fused heteroconjugate molecules (Staerz et al., 1985, Nature 314(6012): 628-31).

Production of e.g. bispecific IgG (BsIgG) by co-expression of the two light and two heavy chains in a single host cell can be highly challenging because of the low yield of desired BsIgG and the difficulty in removing closely related mispaired IgG contaminants (Suresh et al., Proc. Natl. Acad. Sci. U.S.A. 83, 7989-7993, 1986). This reflects that heavy chains form homodimers as well as the desired heterodimers—the heavy chain-pairing problem. Additionally, light chains can mispair with non-cognate heavy chains—the light chain pairing problem. Consequently, coexpression of two antibodies can give rise to up to nine unwanted IgG species in addition to the desired BsIgG.

Engineering antibody heavy chains for heterodimerization has emerged as a successful strategy to overcome the BsIgG heavy chain-pairing problem. The homodimerization of the two heavy chains in an IgG is mediated by the interaction between the $C_H3$ domains alone. Heavy chains were first engineered for heterodimerization in the 1990s using a "knobs-into-holes" strategy. Starting from a "knob" mutation (T366W) (Ridgway et al., 'Protein Eng. 9, 617-621, 1996) that disfavours $C_H3$ homodimerization, compensating "hole" mutations (T366S, L368A, and Y407V) (Atwell et al., J. Mol. Biol. 270, 26-35, 1997) were identified by phage display providing efficient pairing with the "knob" while disfavoring homodimerization. The promiscuity in the IgG domain interface led in recent years to several other successful strategies for heavy chain heterodimerization.

Further, several strategies have been developed to overcome the light chain pairing problem. Light chain mispairing can be obviated by using antibodies with a common light chain identified from phage display libraries with limited light chain diversity (Merchant et al., Nat. Biotechnol. 16, 677-681, 1998). More recently antibodies with a common light chain have been identified from other technologies including transgenic mice with a single light chain (McWhirter et al., WO2011/097603). Currently the most widely used route to BsIgG is by separate expression of the antibody components in two different host cells followed by purification and assembly into BsIgG in vitro (Jackman et al., J. Biol. Chem. 285, 20850-20859, 2010). The major advantage of the two host cell strategies over the common light chain approach is that they are much more broadly applicable to pre-existing antibodies. Moreover, the two different light chains typically contribute to antigen-binding affinity and specificity. Disadvantages of the two-host cell strategies compared to the common light chain are that they are associated with significantly greater expense and complexity in manufacturing.

Disclosed herein are ways to address the light chain pairing problem and achieves the desired paring of the light chains of multispecific antibodies in the same cell with minimal or even without any undesired by-products, i.e. light chain pairings other than the desired ones. This is achieved by using the $C_H2$ domain of an IgM ($MC_H2$) or of an IgE ($EC_H2$) for pairing one light chain variable domain with a heavy chain variable domain as desired and using a different dimerization domain for pairing the other light chain variable domain with a heavy chain variable domain as desired. The function of $MC_H2$ and $EC_H2$ is unknown, very likely they correspond to the hinge region of IgG molecules. The IgM $C_H2$ domain ($MC_H2$) is a 111 amino acid (12.2 kDa) polypeptide forming a homodimer. The dimer has an S—S-bond formed between Cys110 of two domains and an internal S—S-bond between Cys30 and 93 within one domain. $MC_H2$ has a glycosylation site at Asn105. The inventors found that $MC_H2$ domains can be used to replace the $C_H1/C_K$ on one arm of the antibody and discovered the $MC_H2$ fold is as stable as the $C_H1/C_K$ and allows for a correct pairing of the variable domains. This is advantageous in association with modifications facilitating the desired heavy chain pairing. $EC_H2$ is a highly homologous domain with the same function in the IgE antibody and will therefore be just as suitable for this purpose.

Before the detailed description that follows, it is to be understood that the disclosure is not limited to any methodology, protocols and reagents described herein as these may vary. It is also to be understood that the terminology used herein is for the purpose of describing embodiments only, and is not intended to limit the scope of the present invention which will be limited only by the appended claims. Unless defined otherwise, all technical and scientific terms used herein have the same meanings as commonly understood by one of ordinary skill in the art. Specifically, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturers specifications, instructions etc.), whether supra or infra, is hereby incorporated by reference in its entirety. Nothing herein is to be construed as an admission that the invention is not entitled to antedate such disclosure by virtue of prior invention.

In the following, further elements will be described. These elements are listed with specific embodiments; however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In the description that follows, amino acid numbers are used with respect to antibodies, which do not refer to a SEQ ID NO. These numbers refer to amino acid positions in antibodies according to the UniProtKB database (www.uniprot.org/uniprot) in the version as disclosed on Aug. 26, 2016. Unless specified otherwise, the number(s) correspond to a position in human IgG, e.g. in human IgG1. The UniProtKB sequences (in the version as disclosed on Aug. 26, 2016) of antibody domains referred to herein, including those of human IgG1 are incorporated by reference as certain embodiments of the domains described herein, as well as variants thereof as defined below.

In a first aspect, described herein is an antibody heavy chain A, light chain A or dimer thereof, wherein the heavy chain comprises a variable domain $V_HA$ linked to a dimerization domain $CH2_H$ and the light chain comprises a variable domain $V_LA$ linked to a dimerization domain $CH2_L$, and wherein both $CH2_H$ and $CH2_L$ are an IgM constant domain $MC_H2$ or an IgE constant domain $EC_H2$. $MC_H2$ and $EC_H2$ are homologs and have a highly similar amino acid sequence. If $CH2_H$ and $CH2_L$ are an IgM constant domain $MC_H2$, in some embodiments $MC_H2$ comprises a mutation of asparagine 209 to glutamine (position according to the numbering of UniProtKB-P01871 IgHM_HUMAN, as modified on Jul. 1, 2008-v3). If $CH2_H$ and $CH2_L$ are an IgE constant domain $EC_H2$, in some embodiments $EC_H2$ comprises a mutation of cysteine 105 to alanine (avoiding unwanted cysteine reactivity) and/or a mutation of asparagine 146 to glutamine (avoiding glycosylation) (positions according to the numbering of UniProtKB-P01854 IgHE_HUMAN, as modified on Jul. 21, 1986-v1).

In other words, the first aspect can be described as a fragment of an antibody or derivative thereof comprising an antibody heavy chain A, an antibody light chain A or a dimer thereof, as defined above. The term "dimer" refers to a dimer of the heavy chain A and the light chain A.

The term "antibody" as used herein refers to a molecule having the overall structure of an antibody, for example an IgG antibody, which has the light chain-heavy chain dimerization domains replaced by $MC_H2$ or $EC_H2$ domains. It also includes molecules which may have further chimeric domain replacements (i.e. at least one domain replaced by a domain from a different antibody), such as an IgG1 antibody comprising an IgG3 domain (e.g. the $C_H3$ domain of IgG3). Further, the term in some embodiments refers to multispecific, e.g. bispecific or trispecific antibodies. The antibody may alternatively be termed "antibody-like protein" or "chimeric antibody". An example is the "IgG configuration" with constant domains as described herein.

When referring to IgG in general, IgG1, IgG2, IgG3 and IgG4 are included, unless defined otherwise. In certain embodiments, IgG is IgG1.

The term "antibody derivative" as used herein refers to a molecule comprising at least the domains it is specified to comprise, but not having the overall structure of an antibody such as IgA, IgD, IgE, IgG, IgM, IgY or IgW, although still being capable of binding a target molecule. Said derivatives may be, but are not limited to functional (i.e. target binding) antibody fragments thereof such as Fab2, or combinations of such derivatives, for example bivalent Fabs (e.g. as described herein). It also relates to an antibody to which further antibody domains have been added, such as further variable domains. Examples are the "tetravalent bispecific tandem immunoglobulin (TBTI) configuration (also termed and the same as the "dual variable domain configuration"), the "CODV configuration", the "CODV chimera configuration", e.g. the "trivalent configuration", and the "tetravalent spider configuration" as described herein.

The term "heavy chain" as used herein includes also a fragment of a heavy chain that comprises at least a variable domain (in some embodiments of an IgG antibody) linked to a domain for dimerization with a light chain, wherein the dimerization domain is in some embodiments defined more specifically herein when using this term. It may but does not necessarily further comprise a constant domain $C_H2$ and optionally also a constant domain $C_H3$ (in some embodiments both of an IgG antibody). Accordingly, it may also be referred to as "fragment of a heavy chain comprising at least a variable domain linked to a domain for dimerization with a light chain".

In some embodiments and unless one is modified further than the other, $CH2_H$ and $CH2_L$ are identical (i.e. they are homodimerization domains) and in one embodiment each have a sequence according to SEQ ID NO: 1 or according to SEQ ID NO: 2 (these sequences correspond to the CH2 domains used in the examples) or a variant of either with at least 80% sequence identity to SEQ ID NO: 1 or 2, respectively. Compared to human IgM, SEQ ID NO: 1 in some embodiments has a mutation of asparagine to glutamine at position 105 of SEQ ID NO: 1. Thus, a variant of SEQ ID NO: 1 may retain this mutation. Compared to human IgE, SEQ ID NO: 2 in some embodiments has a mutation of cysteine to alanine at position 105 of SEQ ID NO: 2 and/or a mutation of asparagine to glutamine at position 146 of SEQ ID NO: 2. Thus, a variant of SEQ ID NO: 2 may retain one or both of these mutations. Optionally, only one of $CH2_H$ and $CH2_L$ is a variant or the variants of $CH2_H$ and $CH2_L$ differ from each other. In any case, the variants are still capable of dimerization with each other and/or with the domain according to SEQ ID NO: 1 or 2, respectively. A variant has an amino acid sequence that it at least 80%, 85%, 90%, 95%, 96%, 97%, 98% or 99% identical to the amino acid sequence it is derived from, for example SEQ ID NO: 1 or 2. The determination of percent identity between two sequences is accomplished using the mathematical algorithm of Karlin and Altschul, Proc. Natl. Acad. Sci. USA 90, 5873-5877, 1993. Such an algorithm is incorporated into the BLASTN and BLASTP programs of Altschul et al. (1990) J. Mol. Biol. 215, 403-410. To obtain gapped alignments for comparative purposes, Gapped BLAST is utilized as described in Altschul et al. (1997) Nucleic Acids Res. 25, 3389-3402. When utilizing BLAST and Gapped BLAST programs, the default parameters of the respective programs are used. Alternatively, a variant can also be defined as having up to 20, 15, 10, 5, 4, 3, 2, or 1 amino acid substitutions, e.g. conservative amino acid substitutions. Conservative substitutions are well known in the art (see for example Creighton (1984) Proteins. W.H. Freeman and Company). An overview of physical and chemical properties of amino acids is given in Table 1 below. In one embodiment, conservative substitutions are substitutions made with amino acids having at least one property according to Table 1 in common (i.e. of column 1 and/or 2). The term "variant" also includes fragments. A fragment has an N-terminal and/or C-terminal deletion of up to 20, 15, 10, 5, 4, 3, 2, or 1 amino acids in total. In addition to or alternatively, the variant may be modified, for example by N-terminal and/or C-terminal amino acid additions of up to 50, 40, 30, 20, 10, 5, 4, 3, 2, or 1 amino acids in total.

TABLE 1

Properties of naturally occurring proteins.

| Charge properties/ hydrophobicity | Side group | Amino Acid |
| --- | --- | --- |
| nonpolar hydrophobic | aliphatic | Ala, Ile, Leu, Val |
|  | aliphatic, S-containing | Met |
|  | aromatic | Phe, Trp |
|  | imino | Pro |
| polar uncharged | aliphatic | Gly |
|  | amide | Asn, Gln |
|  | aromatic | Tyr |
|  | hydroxyl | Ser, Thr |
|  | sulfhydryl | Cys |
| positively charged | basic | Arg, His, Lys |
| negatively charged | acidic | Asp, Gly |

The term "linked" unless specified otherwise refers to a coupling of two domains by a peptide bond. Therein the two domains may be linked with or without a linker. Herein, it is referred to linking via a linker having a length of 0-X amino acids ("aa"). 0 aa means that the linking is via a peptide bond directly linking the two domains. For this also the term "fused" may be used instead of linked. An X of 1 or larger means that the linking is via a peptide linker. A peptide linker is e.g. a flexible peptide linker, i.e. provides flexibility among the domains that are linked together. Such flexibility is increased if the amino acids are small and do not have bulky side chains that impede rotation or bending of the amino acid chain. Thus, in some embodiments, the peptide linker has an increased content of small amino acids, such as glycine, alanine, serine, threonine, leucine and isoleucine. In certain embodiments, at least 20%, 30%, 40%, 50%, 60% 70%, 80%, 90% or more of the amino acids of the peptide linker are such small amino acids. In one embodiment, the amino acids of the linker are selected from glycines and serines, i.e. said linker is a poly-glycine or a poly-glycine/serine linker, wherein "poly" means a proportion of at least 50%, 60%, 70%, 80%, 90% or even 100% glycine and/or serine residues in the linker. Linkers of CODV configurations as described herein provide sufficient mobility for the domains of the light and heavy chains to fold into cross over dual variable region immunoglobulins. In some embodiments (not limited to CODV configurations), exemplary linkers comprise a sequence of the amino acid formula $(G_mS_n)_o$, wherein m is an integer from 0 to 4, n is 1 or 2, and o is an integer from 0 to 5. Examples are m=1, n=1, o=0-5; m=2, n=1, o=0-5; m=3, n=1, o=0-5; m=4, n=1, o=0-5; m=1, n=2, o=0-5; m=2, n=2, o=0-5; m=3, n=2, o=0-5; and m=4, n=2, o=0-5. If o>1, m and n can each also differ from the m and n, respectively, of one or more further $(G_mS_n)$ reiterations. In other words, for $(G_mS_n)_1$, m and n can differ from m and n, respectively, of any of $(G_mS_n)_{2-5}$. The same is possible for any of $(G_mS_n)_{2-5}$ with respect to the remaining $(G_mS_n)_o$.

Regarding the first aspect, $V_HA$ is linked to $CH2_H$ via a 0-30 aa linker and $V_LA$ is linked to $CH2_L$ via a 0-30 aa linker. Independently or in both cases, the length of each linker may be 1-30, 5-25 or 10-20, e.g. about 15 aa. The two linkers may in some embodiments have the same length and may even be identical, i.e. have the same amino acid sequence. Unless specified otherwise, each linkage referred to herein is by such linker.

In one embodiment, the C-terminus of $V_HA$ is linked (e.g. fused) to the N-terminus of $CH2_H$ and the C-terminus of $V_LA$ is linked (e.g. fused) to the N-terminus of $CH2_L$. Further, $CH2_H$ may be linked via a hinge region to a constant domain $C_H2$, wherein the constant domain $C_H2$ may be fused to a constant domain $C_H3$.

The term "hinge region" as used herein refers to the flexible amino acid stretch in the central part of the heavy chains of the IgG and IgA, e.g. the IgG (i.e. Ig1, IgG2, IgG3 or IgG4, especially IgG1) immunoglobulin classes, which links these two chains by disulfide bonds.

In a further embodiment, the heavy chain A and the light chain A are derived from IgG, e.g. IgG1, IgG2, IgG3 or IgG4. In certain embodiments, they are derived from IgG1, wherein domains therein may be mutated and/or substituted by IgG2, IgG3 or IgG4, e.g. by IgG3 domains, for example as described herein.

In some embodiments, heavy chain A has modifications as described in the second aspect, e.g. one or more modifications facilitating the isolation of the antibody as described.

In a second aspect, the present disclosure relates to an antibody or derivative thereof, comprising a heavy chain A and a light chain A according to the first aspect.

In some embodiments, the antibody or derivative thereof is isolated and/or recombinant. Further, the antibody or derivative thereof may be a mouse antibody, e.g. a humanized mouse antibody, or derivative thereof. Alternatively, the antibody may be derived from any other species, for example from a vertebrate species, e.g. a mammalian species such as a primate species including human, rabbit or rat.

It is envisaged that in the antibody or derivative thereof, in some embodiments the dimerization domain $CH2_H$ and the dimerization domain $CH2_L$ may form a dimer. Furthermore, in one embodiment it is envisaged that $V_HA$ and $V_LA$ form a variable domain $F_VAA$ (i.e. $FvA_HA_L$) and thereby a paratope AA (i.e. $A_HA_L$). In an alternative embodiment, $V_HA$ and $V_LA$ do not form a variable domain $F_VAA$ (or a paratope AA). In some embodiments, instead $V_HA$ forms a variable domain FvAX (i.e. $F_VA_HX_L$), thereby a paratope AX (i.e. $A_HX_L$) with a further light chain variable domain $V_LX$ comprised in light chain A and $V_LA$ forms a variable domain XA (i.e. $F_VX_HA_L$), thereby a paratope XA (i.e. $X_HA_L$)) with a further heavy chain variable domain $V_HX$ comprised in heavy chain A. This alternative is exemplified by the "CODV configuration" as described below (see also FIG. 1 D).

As indicated by these embodiments, the antibody or derivative thereof of the second aspect may be multispecific, e.g. bispecific or trispecific. Accordingly, in some embodiments the antibody or derivative thereof of the second aspect further comprises a heavy chain B and a light chain B, wherein the heavy chain comprises a variable domain $V_HB$ and the light chain comprises a variable domain $V_LB$. These may be arranged with heavy and light chains A in an IgG configuration, i.e. heavy chains A and B dimerize and light chain A dimerizes with heavy chain A and light chain B dimerizes with heavy chain B. Further, the multispecific, e.g. bispecific antibody or derivative thereof may be symmetric or asymmetric. Asymmetric means that the variable domains described above (e.g. $F_VAA$ and FvBB), in certain embodiments the paratopes on the two antibody arms (i.e. of the two heavy chains) are different from each other. Symmetric as used herein means that the antibody or derivative thereof comprises identical variable domains on each arm of an IgG antibody or derivative thereof. A multispecificity of a higher degree than bispecificity is in some embodiments achieved in this antibody by further variable domains on the same arms.

A multispecific antibody or derivative is capable of binding multiple different antigens and a bispecific antibody or derivative is capable of binding two different antigens. For all antibodies or derivatives described herein, the antigen is for example independently selected for each specificity from the group consisting of B7.1, B7.2, BAFF, BlyS, C3, C5, CCL11 (eotaxin), CCL15 (MIP-1d), CCL17 (TARC), CCL19 (MIP-3b), CCL2 (MCP-1), CCL20 (MIP-3a), CCL21 (MIP-2), SLC, CCL24 (MPIF-2/eotaxin-2), CCL25 (TECK), CCL26 (eotaxin-3), CCL3 (MIP-1a), CCL4 (MIP-1b), CCL5 (RANTES), CCL7 (MCP-3), CCL8 (mcp-2), CD3, CD19, CD20, CD24, CD40, CD40L, CD80, CD86, CDH1 (E-cadherin), Chitinase, CSF 1 (M-CSF), CSF2 (GM-CSF), CSF3 (GCSF), CTLA4, CX3CL1 (SCYD1), CXCL12 (SDFI), CXCL13, EGFR, FCER1A, FCER2, HER2, IGF1R, IL-I, IL-12, IL13, IL15, IL17, IL18, IL1A, IL1B, IL1F1O, IL1β, IL2, IL4, IL6, IL7, IL8, IL9, IL12/23, IL22, IL23, IL25, IL27, IL35, ITGB4 (b 4 integrin), LEP (leptin), MHC class II, TLR2, TLR4, TLR5, TNF, TNF-α, TNFSF4 (OX40 ligand), TNFSF5 (CD40 ligand), Toll-like receptors, TREM1, TSLP, TWEAK, XCRI (GPR5/CCXCR1), DNGR-1 (CLEC91), and HMGB1. In certain embodiments, it is from the group consisting of CD3, CD4, CD8, CD28, CD16, NKp46. For all bispecific antibodies or derivatives described herein, the antigen pair is for example selected from the group consisting of the antigen pairs IL4 and IL13, IGF1R and HER2, IGF1R and EGFR, EGFR and HER2, BK and IL13, PDL-1 and CTLA-4, CTLA4 and MHC class II, IL-12 and IL-18, IL-Iα and IL-β, TNFα and IL12/23, TNFα and IL-12p40, TNFα and IL-β, TNFα and IL-23, and IL17 and IL23. For all trispecific antibodies or derivatives described herein, two antigens are for example selected from the group consisting of the antigen pairs IL4 and IL13, IGF1R and HER2, IGF1R and EGFR, EGFR and HER2, BK and IL13, PDL-1 and CTLA-4, CTLA4 and MHC class II, IL-12 and IL-18, IL-Iα and IL-β, TNFα and IL12/23, TNFα and IL-12p40, TNFα and IL-β, TNFα and IL-23, and IL17 and IL23. The third antigen can be another antigen selected from the list above. Further antigens are listed with respect to the sixth aspect below and can also be used for the multispecific antibody or derivative.

An example for a symmetric multispecific antibody is a "tetravalent spider configuration" (see FIG. 1 E), which is defined by the antibody or derivative thereof of the second aspect comprising a first and a second heavy chain A and a first and a second light chain A each according to the first aspect, wherein (i) the $CH2_L$ domain of the first light chain A is linked to the $V_H1$ or $V_L1$ domain (e.g. $V_HB$ or $V_LB$) of an IgG antibody or derivative thereof and the $CH2_L$ domain of the second light chain A is linked to the other $V_H1$ or $V_L1$ domain (e.g. $V_HB$ or $V_LB$) of the IgG antibody or derivative thereof (for example in both cases to the $V_H1$ domain or to the $V_L1$ domain), or (ii) the $CH2_H$ domain of the first light chain A is linked to the $V_H1$ or $V_L1$ domain (e.g. $V_HB$ or $V_LB$) of an IgG antibody or derivative thereof and the $CH2_H$ domain of the second light chain A is linked to the other $V_H1$ or $V_L1$ domain (e.g. $V_HB$ or $V_LB$) of the IgG antibody or derivative thereof (for example in both cases to the $V_H1$ domain or to the $V_L1$ domain). In this respect, the linkage is in some embodiments via a 0-10 aa linker. Independently, the length of each linker may be 1-10 or 2-6 aa. In certain embodiments, the two linkers may have the same length and may even be identical, i.e. have the same amino acid sequence. A "derivative" of an IgG antibody in this respect is in certain embodiments an antigen-binding IgG fragment such as a Fab2 fragment.

In the "tetravalent spider configuration", in some embodiments the $CH2_L$ domain of the first light chain A forms a dimer with the $CH2_H$ domain of the first heavy chain A and the $CH2_L$ domain of the second light chain A forms a dimer with the $CH2_H$ domain of the second heavy chain A. Furthermore, in some embodiments $V_HA$ and $V_LA$ of the first heavy and light chains A form a variable domain $F_VAA$ (i.e. $FvA_HA_L$), thereby a paratope AA (i.e. $A_HA_L$), and $V_HA$ and $V_LA$ of the second heavy and light chains A form a variable domain $F_VAA$ (i.e. $FvA_HA_L$), thereby a paratope AA (i.e. $A_HA_L$). Further, the $V_H1$ and $V_L1$ domains of the IgG part are also symmetric, i.e. they form one variable domain $F_V$ each which is the same for both (e.g. $F_VBB$).

An asymmetric multispecific antibody or derivative thereof, e.g. an asymmetric bispecific antibody or derivative thereof, in some embodiments comprises a heavy chain B and a light chain B, wherein the heavy chain comprises a variable domain $V_HB$ and the light chain comprises a variable domain $V_LB$.

Examples of this asymmetric antibody or derivative thereof are the "bivalent Fab configuration" (see FIG. 1 B) and the "IgG configuration" (see FIG. 1 A). Therein, $V_HB$ is linked to a dimerization domain $DIM_H$ and $V_LB$ is linked to a dimerization domain $DIM_L$. In the "bivalent Fab configuration", the two Fabs may be linked to each other via the $CH2_H$ and the $DIM_H$ domains as shown in FIG. 1B, or one of the DIM domains may be linked to one of the VA domains (e.g. $DIM_H$ to $V_HA$), or one of the CH2 domains may be linked to one of the VB domains (e.g. VH2$_H$ to V$_H$B). In this respect, the linkage is in some embodiments via a 0-30 or 1-30 aa linker. Independently, the length of each linker may be 5-25 or 10-20, e.g. about 15 aa. In certain embodiments, the two linkers have the same length and may even be identical, i.e. have the same amino acid sequence.

The term "DIM" is not used herein as an art known term for an antibody domain, but as a designation for a dimerization domain, in certain embodiments a homodimerization domain. DIM$_H$ and DIM$_L$ in some embodiments form a dimer. Also, DIM$_H$ and DIM$_L$ are not constant domains C$_H$2, i.e. they are different from the pair CH2$_H$ and CH2$_L$. In certain embodiments, they are not an IgM constant domain MC$_H$2 or an IgE constant domain EC$_H$2. In one embodiment, a DIM domain is derived from an antibody. In a specific embodiment, DIM$_H$ and DIM$_L$ are C$_{H1}$ and C$_L$, respectively, of an IgG antibody. Furthermore, it is envisaged that both the heavy chain B and the light chain B are derived from IgG, unless specified otherwise. In certain embodiments, the antibody or derivative thereof is bispecific. It is also envisaged that V$_H$A and V$_L$A may form a variable domain F$_V$AA (i.e. FvA$_H$A$_L$), in certain embodiments a paratope AA (i.e. A$_H$A$_L$), and V$_H$B and V$_L$B form a variable domain F$_V$BB (i.e. FvB$_H$B$_L$), in certain embodiments a paratope BB (i.e. B$_H$B$_L$)).

In the "bivalent Fab configuration", in some embodiments DIM$_H$ is linked to CH2$_H$ or CH2$_L$, or DIM$_L$ is linked to CH2$_H$ or CH2$_L$. Alternatively, one of the DIM domains may be linked to one of the VA domains (e.g. DIM$_H$ to V$_H$A), or one of the CH2 domains may be linked to one of the VB domains (e.g. VH2$_H$ to V$_H$B). In this respect, the linkage is in some embodiments via a 0-30 or 1-30 aa linker. The length of the linker may be 5-25 or 10-20, e.g. about 15 aa.

In the "IgG configuration", in some embodiments CH2$_H$ is linked via a hinge region to a constant domain C$_H$2A and DIM$_H$ is linked via a hinge region to a constant domain C$_H$2B. C$_H$2A may be linked, (e.g. fused) to a constant domain C$_H$3A and C$_H$2B may be linked (e.g. fused) to a constant domain C$_H$3B. Further, it is contemplated that heavy chain A is bound to heavy chain B via disulfide bonds (in some embodiments, for example, via two disulfide bonds) between the hinge region of heavy chain A and the hinge region of heavy chain B. Alternatively, in the IgG configuration, CH2$_H$ is not linked via a hinge region to a constant domain C$_H$2A and DIM$_H$ is not linked via a hinge region to a constant domain C$_H$2B, but CH2$_H$ is linked to a different CH2$_H$ domain (e.g. a ECH2$_H$ domain if the CH2$_H$ of the Fab domain is an MCH2$_H$ domain, or vice versa), and DIM$_H$ is linked to a CH2$_H$ domain capable of pairing with that different CH2H domain, in certain embodiments to a CH2$_H$ domain that is the same (in as of the same type) as that different CH2$_H$ domain (e.g. an ECH2$_H$ domain if the other CH2$_H$ domain is an ECH2$_H$ domain; or an MCH2$_H$ domain if the other CH2$_H$ domain is an MCH2$_H$ domain).

Another example of the asymmetric antibody or derivative thereof described above is the "TBTI configuration" (see FIG. 1 C). It is configured as the "IgG configuration", but in addition
  heavy chain A further comprises a further heavy chain variable domain V$_H$X linked to V$_H$A,
  light chain A further comprises a further light chain variable domain V$_L$X linked to V$_L$A,
  heavy chain B further comprises a further heavy chain variable domain V$_H$Y linked to V$_H$B, and
  light chain B further comprises a further light chain variable domain V$_L$Y linked to V$_L$B.

These linkages are via a 0-15 aa linker, such as a 1-15 aa linker each. Independently, the length of each linker may be 5-10 or about 7 or 8 aa. In some embodiments, the linkers have the same length and may even be identical, i.e. have the same amino acid sequence. In one embodiment, the C-termini of V$_H$X, V$_L$X, V$_H$Y and V$_L$Y are fused to N-termini of V$_H$A, V$_L$A, V$_H$B and V$_L$B, respectively. For this configuration, it is contemplated that
  V$_H$A and V$_L$A form a variable domain F$_V$AA (i.e. FvA$_H$A$_L$), thereby a paratope AA (i.e. A$_H$A$_L$),
  V$_H$B and V$_L$B form a variable domain F$_V$BB (i.e. FvB$_H$B$_L$), thereby a paratope BB (i.e. B$_H$B$_L$),
  V$_H$X and V$_L$X form a variable domain F$_V$XX (i.e. FvX$_H$X$_L$), thereby a paratope XX (i.e. X$_H$X$_L$), and
  V$_{HY}$ and V$_L$Y form a variable domain F$_V$YY (i.e. FvY$_H$Y$_L$), thereby a paratope YY (or Y$_H$Y$_L$).

Yet another example of the asymmetric antibody or derivative thereof described above is the "cross-over dual variable configuration" or "CODV configuration". An example of a CODV configuration is described in WO 2012/135345 A1 and comprises like the "TBTI configuration" a
  heavy chain A comprising a further heavy chain variable domain V$_H$X linked to V$_H$A,
  light chain A comprising a further light chain variable domain V$_L$X linked to V$_L$A,
  heavy chain B comprising a further heavy chain variable domain V$_H$Y linked to V$_H$B, and
  light chain B comprising a further light chain variable domain V$_L$Y linked to V$_L$B.

In one embodiment, the C-termini of V$_H$X, V$_L$X, V$_H$Y and V$_L$Y are fused to N-termini of V$_H$A, V$_L$A, V$_H$B and V$_L$B, respectively However, in the "CODV configuration",
  V$_H$A forms a variable domain FvAX (i.e. F$_V$A$_H$X$_L$), thereby a paratope AX (i.e. A$_H$X$_L$)) with V$_L$X,
  V$_L$A forms a variable domain FvXA (i.e. F$_V$X$_H$A$_L$), thereby a paratope XA (i.e. X$_H$A$_L$)) with V$_H$X,
  V$_H$B forms a variable domain FvBY (i.e. F$_V$B$_H$Y$_L$), thereby a paratope (i.e. B$_H$Y$_L$)) with V$_L$Y,
  V$_L$B forms a variable domain YB (i.e. F$_V$Y$_H$B$_L$), thereby a paratope YB (i.e. Y$_H$B$_L$)) with V$_{HY}$.

Thus, unlike in the "TBTI configuration", V$_H$A and V$_L$A, V$_H$B and V$_L$B, V$_H$X and V$_L$X, V$_H$Y and V$_L$Y do not form paratopes AA, BB, XX, YY, respectively.

This is achieved by the following linkages (L1: linker 1, L2: linker 2, L3: linker 3, L4: linker 4):
  (i)
  CH2$_H$ to V$_H$A by a 1-3 aa or 1-2 aa, or about 2 aa linker, alternatively 0 aa linker (L4),
  CH2$_L$ to V$_L$A by a 3-14 aa or 5-8 aa, or about 5 aa linker, alternatively 10 aa linker (L2),
  DIM$_H$ to V$_H$B by a 1-3 aa or 1-2 aa, or about 2 aa linker, alternatively 0 aa linker (L4),
  DIM$_L$ to V$_L$B by a 3-14 aa or 5-8 aa, or about 5 aa linker, alternatively 10 aa linker (L2),
  V$_H$A to V$_H$X by a 1-8 aa or 1-5 aa, or about 1 aa linker, alternatively 0 aa linker (L3),
  V$_L$A to V$_L$X by a 3-12 aa or 5-10 aa, or about 7 aa linker, alternatively 10 aa linker (L1),
  V$_H$B to V$_H$Y by a 1-8 aa or 1-5 aa, or about 1 aa linker, alternatively 0 aa linker (L3), and
  V$_L$B to V$_L$Y by a 3-12 aa or 5-10 aa, or about 7 aa linker, alternatively 10 aa linker (L1); or
  (ii)
  CH2$_H$ to V$_H$A by a 2-15 aa or 2-12 aa, or about 5 aa linker, alternatively 10 aa linker (L4), CH2$_L$ to V$_L$A by a 1-4 aa or 1-2 aa, or about 2 aa linker, alternatively 0 aa linker (L2), DIM$_H$ to V$_H$B by a 2-15 aa or 2-12 aa, or about 5 aa linker, alternatively 10 aa linker (L4), DIM$_L$ to V$_L$B by a 1-4 aa or 1-2 aa, or about 2 aa linker, alternatively 0 aa linker (L2), V$_H$A to V$_H$X by a 2-15 aa or 4-12 aa, or about 7 aa linker, alternatively 10 aa linker (L3), V$_L$A to V$_L$X by a 1-3 aa or 1-2 aa, or about 1 aa linker, alternatively 0 aa linker (L1), V$_H$B to V$_H$Y by a 2-15 aa or 4-12 aa, or about 7 aa linker, alternatively 10 aa linker (L3), and V$_L$B to V$_L$Y by a 1-3 aa or 1-2 aa, or about 1 aa linker, alternatively 0 aa linker (L1).

In (i) above, the light chain linkers are longer than the heavy chain linkers on both arms, and in (ii) above, the heavy chain linkers are longer than the light chain linkers on both arms. In other words, with respect to the linkers, the arms are symmetric. However, they can also be asymmetric as indicated in FIG. 1D, i.e. on one arm, the light chain linkers are longer than the heavy chain linkers and on the other arm the heavy chain linkers are longer than the light chain linkers. This results directly in the following alternative embodiments (iii) and (iv), respectively:

(iii)
CH2$_H$ to V$_H$A by a 1-3 aa or 1-2 aa, or about 2 aa linker, alternatively 0 aa linker (L4), CH2$_L$ to V$_L$A by a 3-14 aa or 5-8 aa, or about 5 aa linker, alternatively 10 aa linker (L2), DIM$_H$ to V$_H$B by a 3-14 aa or 5-8 aa, or about 5 aa linker, alternatively 10 aa linker (L4), DIM$_L$ to V$_L$B by a 1-3 aa or 1-2 aa, or about 2 aa linker, alternatively 0 aa linker (L2), V$_H$A to V$_H$X by a 1-8 aa or 1-5 aa, or about 1 aa linker, alternatively 0 aa linker (L3), V$_L$A to V$_L$X by a 3-12 aa or 5-10 aa, or about 7 aa linker, alternatively 10 aa linker (L1), V$_H$B to V$_H$Y by a 3-12 aa or 5-10 aa, or about 7 aa linker, alternatively 10 aa linker (L3), and V$_L$B to V$_L$Y by a 1-8 aa or 1-5 aa, or about 1 aa linker, alternatively 0 aa linker (L1); or (iv)
CH2$_H$ to V$_H$A by a 2-15 aa or 2-12 aa, or about 5 aa linker, alternatively 10 aa linker (L4), CH2$_L$ to V$_L$A by a 1-4 aa or 1-2 aa, or about 2 aa linker, alternatively 0 aa linker (L2), DIM$_H$ to V$_H$B by a 1-4 aa or 1-2 aa, or about 2 aa linker, alternatively 0 aa linker (L4), DIM$_L$ to V$_L$B by a 2-15 aa or 2-12 aa, or about 5 aa linker, alternatively 10 aa linker (L2), V$_H$A to V$_H$X by a 2-15 aa or 4-12 aa, or about 7 aa linker, alternatively 10 aa linker (L3), V$_L$A to V$_L$X by a 1-3 aa or 1-2 aa, or about 1 aa linker, alternatively 0 aa linker (L1), V$_H$B to V$_H$Y by a 1-3 aa or 1-2 aa, or about 1 aa linker, alternatively 0 aa linker (L3), and V$_L$B to V$_L$Y by a 2-15 aa or 4-12 aa, or about 7 aa linker, alternatively 10 aa linker (L1).

In the above, any range can be combined with another. In some embodiments, the most general ranges can be combined with each other, or the smaller ranges with each other, or the single values mentioned last with each other (first alternatives which each other and second alternative with each other). With respect to (i), in some embodiments the CH2$_L$ to V$_L$A and DIM$_L$ to V$_L$B linkers are longer than the CH2$_H$ to V$_H$A and DIM$_H$ to V$_H$B linkers, respectively, and the V$_L$X to V$_L$A and V$_L$Y to V$_L$B linkers are longer than the V$_H$A to V$_H$X and V$_H$B to V$_H$Y linkers, respectively. With respect to (ii), in some embodiments the CH2$_H$ to V$_H$A and DIM$_H$ to V$_H$B linkers are longer than the CH2$_L$ to V$_L$A and DIM$_L$ to V$_L$B linkers, respectively, and the V$_H$A to V$_H$X and V$_H$B to V$_H$Y linkers are longer than the V$_L$X to V$_L$A and V$_L$Y to V$_L$B linkers, respectively. With respect to (iii), in some embodiments the CH2$_L$ to V$_L$A and DIM$_H$ to V$_H$B linkers are longer than the CH2$_H$ to V$_H$A and DIM$_L$ to V$_L$B linkers, respectively, and the V$_L$X to V$_L$A and V$_H$Y to V$_H$B linkers are longer than the V$_H$A to V$_H$X and V$_L$B to V$_L$Y linkers, respectively. With respect to (iv), in some embodiments the CH2$_H$ to V$_H$A and DIM$_L$ to V$_L$B linkers are longer than the CH2$_L$ to V$_L$A and DIM$_H$ to V$_H$B linkers, respectively, and the V$_H$A to V$_H$X and V$_L$B to V$_L$Y linkers are longer than the V$_L$X to V$_L$A and V$_H$Y to V$_H$B linkers, respectively. Longer herein may mean at least 1.5 times as long, at least 1.75 times as long or at least 2 times as long (in as far as possible given the specified ranges).

Further, the above can also be described with heavy (I) and light chain (II) domain formulas for each arm, which are
(I) CH2$_H$/DIM$_H$-L4-V$_H$-L3-V$_H$ and (II) CH2$_L$/DIM$_L$-L2-V$_L$-L1-V$_L$,
wherein one arm has CH2$_H$ and CH2$_L$ for (I) and (II), respectively, and the other arm has DIM$_H$ and DIM$_L$ for (I) and (II), respectively,
and wherein L4 is (a) a 1-3 aa or 1-2 aa, or about 2 aa linker, alternatively 0 aa linker, or (b) a 2-15 aa or 2-12 aa, or about 5 aa linker, alternatively 10 aa linker, L3 is (a) a 1-8 aa or 1-5 aa, or about 1 aa linker, alternatively 0 aa linker, or (b) a 2-15 aa or 4-12 aa, or about 7 aa linker, alternatively 10 aa linker, L2 is (a) a 3-14 aa or 5-8 aa, or about 5 aa linker, alternatively 10 aa linker, or (b) a 1-4 aa or 1-2 aa, or about 2 aa linker, alternatively 0 aa linker. Therein, embodiments (a) can combine with each other, and embodiments (b) can combine with each other. Also, the most general ranges are in some embodiments combined with each other, or the smaller ranges with each other, or the single values mentioned last with each other (first alternatives which each other and second alternative with each other).

One specific embodiment of the "CODV configuration" is the "CODV bivalent Fab configuration", which comprises the left "A" arm of the "CODV configuration" shown in FIG. 1D without the constant domains C$_H$2A and C$_H$3A, i.e. it comprises the domains V$_H$A, V$_L$A, V$_H$X and V$_L$X configured as described for the "CODV configuration".

A further example of an asymmetric antibody or derivative thereof described above is the "CODV chimera configuration" with an example being the "trivalent configuration" (see FIG. 1 F). In the "CODV chimera configuration", the antibody comprises one arm A not in the "CODV configuration" and one arm B in the "CODV configuration". Either the arm A comprises CH2 domains as described herein and the arm B comprises DIM domains as described herein, or the arm A comprises the DIM domains and arm B the CH2 domains.

The arm A not in the "CODV configuration" can have any antibody arm configuration, including an arm of configurations described herein, e.g. of asymmetric configurations described herein, such as the "IgG configuration" or the "TBTI configuration". In the arm A in the "IgG configuration", the heavy chain and the light chain are configured as described above for that configuration (with CH2 domains if arm B comprises DIM domains or with DIM domains instead if arm B comprises CH2 domains). In the arm A in the "TBTI configuration", the heavy chain and the light chain are configured as described above for that configuration (with CH2 domains if arm B comprises DIM domains or with DIM domains instead if arm B comprises DH2 domains).

The arm B in the "CODV configuration" is configured as defined as described above for that configuration (with DIM domains if arm A comprises CH2 domains or with CH2 domains instead if arm A comprises DIM domains). The linkage of the domains can be either as in (i) or (ii) defined above.

The embodiment with arm A having the "IgG configuration" is a certain configuration also termed "trivalent configuration" herein (see FIG. 1 F) as it forms three paratopes. This configuration can be monospecific (all paratopes are the same), but is in some embodiments bispecific (two of the three paratopes are same) or trispecific (all paratopes are different).

In further embodiments of the multispecific, e.g. bispecific antibody or derivative thereof of the second aspect, the antibody or derivative thereof comprises one or more modifications facilitating the isolation of the antibody, especially modifications facilitating the pairing of heavy chain A with heavy chain B or allowing for the selection of this pairing. This applies e.g. to an asymmetric antibody or derivative of the second aspect.

For example, the modifications facilitating the isolation of the antibody may be one or more of the following: a knobs into holes technology modification, a DuoBody technology modification, an Azymmetric technology modification, a Charge Pair technology modification, a HA-TF technology modification, a SEEDbody technology modification or a Differential protein A affinity modification. In some embodiments, they may be one or more of the following:

first heavy chain (e.g. heavy chain A): T366Y mutation and optionally further S354C and/or T166W mutation, second heavy chain (e.g. heavy chain B): Y407T mutation and optionally further Y349C, T366S, L368A and/or Y407V mutation (knobs into holes technology), first heavy chain (e.g. heavy chain A): T366W mutation, second heavy chain (e.g. heavy chain B): T366S, L368A and/or Y407V mutation (knobs into holes technology), first heavy chain (e.g. heavy chain A): F405L mutation, second heavy chain (e.g. heavy chain B): K409R mutation (DuoBody technology), first heavy chain (e.g. heavy chain A): T350V, L351Y, F405A and Y407V mutation, second heavy chain (e.g. heavy chain B): T350V, T366L, K392L and T394W mutation (Azymmetric technology), first heavy chain (e.g. heavy chain A): K409D and K392D mutation, second heavy chain (e.g. heavy chain B): D399K and E356K mutation (Charge Pair technology), first heavy chain (e.g. heavy chain A): D221E, P228E and L368E mutation, second heavy chain (e.g. heavy chain B): D221R, P228R and K409R mutation (Charge Pair technology), first heavy chain (e.g. heavy chain A): S364H and F405A mutation, second heavy chain (e.g. heavy chain B): Y349T and T394F mutation (HA-TF technology), first heavy chain (e.g. heavy chain A): IgG/A chimera, second heavy chain (e.g. heavy chain B): IgA/G chimera (SEEDbody technology), first heavy chain (e.g. heavy chain A): Fc region or part thereof (e.g. $C_H3$ domain) is from IgG3, second heavy chain (e.g. heavy chain B) Fc region or part thereof (e.g. $C_H3$ domain) is from IgG1, 2 or 4 (Differential protein A affinity), first heavy chain (e.g. heavy chain A): H435R and Y436F mutation, second heavy chain (e.g. heavy chain B): T407T mutation (Differential protein A affinity), and/or first heavy chain (e.g. heavy chain A): H435R mutation, second heavy chain (e.g. heavy chain B): no mutation (Differential protein A affinity).

Therein, the first heavy chain may alternatively be heavy chain B and the second heavy chain may be heavy chain A.

In one embodiment, the antibody has a Y-shaped IgG like form (including the "IgG configuration", the "TBTI configuration" and the "CODV configuration"), the constant domains $C_H2A$, $C_H2B$, $C_H3A$ and/or $C_H3B$, in certain embodiments $C_H3A$ and/or $C_H3B$, facilitate heavy chain heterodimerization or a selection of heavy chain heterodimers. By heavy chain heterodimerization a linkage of heavy chain A to heavy chain B is meant, so a linkage of heavy chain A to a further heavy chain A and/or a linkage of chain B to a further heavy chain B is impeded or selected against.

For example, the Fc regions of heavy chain A and heavy chain B (e.g. constant domains $C_H2A$ and $C_H2B$, and/or $C_H3A$ and $C_H3B$), e.g. $C_H3A$ and $C_H3B$ comprise knob-into-hole mutations. Such knob-into-hole mutations are e.g. T366Y in one of $C_H3A$ or $C_H3B$ and Y407T in the other, wherein $C_H3A$ and $C_H3B$ are IgG1 constant domains, and optionally wherein the Fc region comprising the T366Y mutation ("knob" chain) further comprises the mutations S354 and T166W and the Fc region comprising the Y407T mutation ("hole" chain) further comprises the mutations Y349C, T366S, L368A and Y407V.

Alternatively or in addition, (i) either the Fc region of heavy chain A or a part thereof (e.g. $C_H2A$ or $C_H3A$), e.g. $C_H3A$, or the Fc region of heavy chain B or a part thereof (e.g. $C_H2B$ or $C_H3B$), e.g. $C_H3B$, is derived from IgG3, or (ii) either the Fc region of heavy chain A (i.e. $C_H2A$ and $C_H3A$), e.g. $C_H3A$, or the Fc region of heavy chain B (i.e. $C_H2B$ and $C_H3B$), e.g. $C_H3B$, comprises one or more mutations decreasing, e.g. abolishing the binding to Protein A. Such mutations may be H435R and Y436F in either $C_H3A$ or $C_H3B$, wherein $C_H3A$ and $C_H3B$ are IgG1 constant domains.

It is envisaged that the Fc regions of heavy chain A and heavy chain B (e.g. constant domains CH2A and $C_H2B$, and/or $C_H3A$ and $C_H3B$), e.g. $C_H3A$ and $C_H3B$ comprise knob-into-hole mutations and either the Fc region of heavy chain A (i.e. $C_H2A$ and $C_H3A$), e.g. $C_H3A$, or the Fc region of heavy chain B (i.e. $C_H2B$ and $C_H3B$), e.g. $C_H3B$, comprises one or more mutations abolishing the binding to Protein A. It is also envisaged that the heavy chain comprising the hole mutation(s) of the knob-into-hole mutations comprises the one or more mutations decreasing, e.g. abolishing the binding to Protein A. This has the advantage that the isolation of this antibody can be performed without a Kappa Select chromatography as described below, since the knob-into-hole approach allows for dimerization also of two "hole" heavy chains, but not for dimerization of two "knob" heavy chains. Therefore, if the "hole" heavy chain has the one or more mutations decreasing, e.g. abolishing the binding to Protein A and it is selected with Protein A chromatography, one will select against the "hole" dimers and isolate only the multispecific, e.g. bispecific antibody without any further steps.

Further, the antibody or derivative thereof of the second aspect may have reduced or no Fc effector functions. An Fc effector function is the interaction with complement protein C1q and/or the binding to Fc receptors. A reduced or a lack of effector functions can be achieved for example by a double mutation L234A and L235A (so-called "LALA mutation") in the $C_H2A$ and/or the $C_H2B$ domain.

All terms used with respect to the second aspect have the meanings as defined with respect to the first aspect, unless specifically defined otherwise. Further, all embodiments specified for the first aspect that are applicable to the second aspect are also envisaged for the second aspect.

In a third aspect, described herein are one or more polynucleotides encoding for the heavy chain A and/or the light chain A of the first aspect. In one embodiment, the one or more polynucleotides also encode for the heavy chain B and/or for the light chain B of the antibody or derivative of the second aspect. In some embodiments, the one or more polynucleotides encode for the antibody or derivative of the second aspect. This refers to all embodiments described above, such as any of the antibody configurations described herein. In one embodiment, the one or more polynucleotides are isolated.

All terms used with respect to the third aspect have the meanings as defined with respect to the first and second aspect, unless specifically defined otherwise. Further, all embodiments specified for the first and second aspect that are applicable to the third aspect are also envisaged for the third aspect.

In a fourth aspect, described herein are one or more expression vectors comprising the one or more polynucleotides of the third aspect.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been fused. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes they comprise. Such vectors are referred to herein as "expression vectors".

All embodiments specified for the first, second and third aspect that are applicable to the fourth aspect are also envisaged for the fourth aspect.

In a fifth aspect, described herein is a cell comprising the one or more polynucleotides of the third aspect or the one or more expression vectors of the fourth aspect. In one embodiment, the cell is isolated.

A wide variety of cell expression systems can be used to express said polynucleotides including the use of prokaryotic and eukaryotic cells, such as bacterial cells (e.g. *E. coli*), yeast cells, insect cells or mammalian cells (e.g. mouse cells, rat cells, human cells etc.). For this purpose, a cell is transformed or transfected with said polynucleotide(s) or expression vector(s) such that the polynucleotide(s) are expressed in the cell and, in one embodiment, secreted into the medium in which the cells are cultured, from where the expression product can be recovered.

All embodiments specified for the first, second, third and fourth aspect that are applicable to the fifth aspect are also envisaged for the fifth aspect.

A sixth aspect relates to a pharmaceutical composition comprising a pharmaceutically acceptable carrier and a dimer of the heavy chain A and the light chain A of the first aspect or the antibody or derivative of the second aspect, wherein in a certain embodiment the dimer or the antibody or derivative specifically binds to a pathogen, a diseased cell, a cell receptor or a cell signalling molecule.

The pharmaceutical compositions described herein can be selected for parenteral delivery. Alternatively, the compositions can be selected for inhalation or for delivery through the digestive tract, such as orally. The preparation of such pharmaceutically acceptable compositions is within the skill of the art.

The term "pharmaceutically acceptable carrier" or "physiologically acceptable carrier" as used herein refers to one or more formulation materials suitable for accomplishing or enhancing the delivery of an antibody-like binding protein. The primary carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment, antibody-like binding protein compositions can be prepared for storage by mixing the selected composition having the desired degree of purity with optional formulation agents in the form of a lyophilized cake or an aqueous solution. Further, the antibody-like binding protein can be formulated as a lyophilizate using appropriate excipients such as sucrose.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediaminetetraacetic acid (EDTA)), complexing agents (such as caffeine, polyvinylpyrrolidone, beta-cyclodextrin, or hydroxypropylbeta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides, in certain embodiments sodium or potassium chloride—or mannitol sorbitol), delivery vehicles, diluents, excipients and/or pharmaceutical adjuvants (see, e.g., REMINGTON's PHARMACEUTICAL SCIENCES (18th Ed., A. R. Gennaro, ed., Mack Publishing Company 1990), and subsequent editions of the same).

The term "specifically binds" as used herein refers to a binding reaction which is determinative of the presence of the target molecule in vitro or in vivo, e.g. in an organism such as the human body. As such, the specified ligand binds to its target molecule and does not bind in a substantial amount to other molecules present. In some embodiments, an antibody or derivative thereof that "specifically binds" a target molecule has an equilibrium affinity constant greater than about $10^5$ (e.g., $10^6$, $10^7$, $10^8$, $10^9$, $10^{10}$, $10^{11}$, and $10^{12}$ or more) mole/liter for that target molecule.

The term "pathogen" refers to any organism which may cause disease in a subject. It includes but is not limited to bacteria, protozoa, fungi, nematodes, viroids and viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms which may not ordinarily be pathogenic in a non-immunocompromised host, but are in an immunocompromised host.

The diseased cell may be a tumor cell, a chronically infected cell, a senescent cell, a cell showing an inflammatory phenotype, a cell accumulating amyloid proteins or a cell accumulating misfolded proteins.

In case of a tumor cell, the underlying disease is a tumor, e.g. selected from the group consisting of Adrenal Cancer, Anal Cancer, Bile Duct Cancer, Bladder Cancer, Bone Cancer, Brain/CNS, Tumors, Breast Cancer, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldnstrom Macroglobulinemia, and Wilms Tumor. In some embodiments, the antigen is a cancer associated antigen, such as HER2, EGFR, EGFRvIII, EGFR3 (ERBB3), MET, FAP, PSMA, CXCR4, ITGB3, CEA, CAIX, Mucins, Folate-binding protein, GD2, VEGFR1, VEGFR2, CD20, CD30, CD33, CD52, CTLA4, CD55, integrin $\alpha V \beta 3$, integrin $\alpha 5 \beta 1$, IGF1R, EPHA3, RANKL, TRAILR1, TRAILR2, IL13Ralpha, UPAR, Tenascin, PD-1, PD-L1, Tumor-associated glycoprotein 72, Ganglioside GM2, A33, Lewis Y antigen or MUC1.

In case of a chronically infected cell, the underlying disease is a chronic infectious disease, such as tuberculosis, malaria, chronic viral hepatitis (HBV, Hepatitis D virus and HCV), Acquired immune deficiency syndrome (AIDS, caused by HIV, Human Immunodeficiency Virus), or EBV related disorders: Systemic Autoimmune Diseases (Systemic Lupus Erithematosus, Rheumatoid Arthritis, and Sjogren Syndrome) and Multiple Sclerosis (MS). In some embodiments, the chronically infected cell comprises a pathogen or part thereof of the above-recited infectious diseases.

In case of a senescent cell, the underlying disease is a senescence associated disease, such as (i) Rare genetic diseases called Progeroid syndromes, characterized by premature aging: Werner syndrome (WS), Bloom syndrome (BS), Rothmund-Thomson syndrome (RTS), Cockayne syndrome (CS), Xeroderma pigmentosum (XP), Trichothiodystrophy or Hutchinson-Gilford Progeria Syndrome (HGPS) or (ii) Common age related disorders: Obesity, type 2 diabetes, sarcopenia, osteoarthritis, idiopathic pulmonary fibrosis and chronic obstructive pulmonary disease, cataracts, neurodegenerative diseases, or cancer treatment related disorders. In some embodiments, the senescent cell expresses, e.g. in a misfolded form and/or presented on the cell surface, one or more protein such as prion protein (PrP), FasR, Fas ligand, CD44, EGF receptor, CD38, Notch-1, CD44, CD59, or TNF receptor. Notwithstanding, the cell may also be a non-diseased cell expressing one or more of these proteins.

In case of a cell showing an inflammatory phenotype, the underlying disease is an inflammatory disease, such as an Allergy, Asthma, Artherosclerosis, Autoimmune diseases, Autoinflammatory diseases, Celiac disease, Chronic prostatitis, Glomerulonephritis, Hypersensitivities, Inflammatory Bowel disease, Inflammatory myopathies, Obesity, Pelvic inflammatory disease, Reperfusion injury, Rheumatoid arthritis, Sarcoidosis, Transplant rejection, Vasculitis, or Interstitial cystitis. In some embodiments, a cell showing an inflammatory phenotype is a cell overexpressing one or more proinflammatory factors such as Bradykinin, C3, C5a, Factor XII, Membrane attack complex, Plasmin, Thrombin, Lysosome granules, Histamine, IFN-gamma, IL-8, IL-6, IL-8, IL-18, Leukotriene B4, Nitric oxide, Prostaglandins, TNF-alpha, or C-reactive Protein.

In case of a cell accumulating amyloid proteins, the underlying disease is a disease associated with the abnormal accumulation of amyloid fibrils such as Alzheimer's disease, Diabetes mellitus type 2, Parkinson's disease, Transmissible spongiform encephalopathy, Fatal familial insomnia, Huntington's disease, Medullary carcinoma of the thyroid, Cardiac arrythmias, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Lattice corneal dystrophy, Cerebral amyloid angiopathy Cerebral amyloid angiopathy, Systemic AL amyloidosis, or Sporadic inclusion body myositis. In some embodiments, a cell accumulating amyloid proteins is a cell overexpressing one or more amyloids such as Beta amyloid, IAPP, Alpha-synuclein, $PrP^{Sc}$, Huntingtin, Calcitonin, Atrial natriuretic factor, Apolipoprotein A1, Serum amyloid A, Medin, Prolactin, Transthyretin, Lysozyme, Beta-2 microglobulin, Gelsolin, Keratoepithelin, Cystatin, Immunoglobulin light chain AL, or S-IBM.

In case of a cell accumulating misfolded proteins, the underlying disease is a proteopathy such as Alzheimer's disease, Cerebral β-amyloid angiopathy, Retinal ganglion cell degeneration in glaucoma, Prion diseases, Parkinson's disease, Tauopathies, Frontotemporal lobar degeneration, FTLD-FUS, Amyotrophic lateral sclerosis, Huntington's disease, Familial British dementia, Familial Danish dementia, Hereditary cerebral hemorrhage with amyloidosis, CADASIL, Alexander disease, Seipinopathies, Familial amyloidotic neuropathy, Senile systemic amyloidosis, AL (light chain) amyloidosis, AH (heavy chain) amyloidosis, AA (secondary) amyloidosis, Type II diabetes, Aortic medial amyloidosis, ApoAI amyloidosis, ApoAII amyloidosis, ApoAIV amyloidosis, Familial amyloidosis of the Finnish type, Lysozyme amyloidosis, Fibrinogen amyloidosis, Dialysis amyloidosis, Inclusion body myositis/myopathy, Cataracts, Retinitis pigmentosa with rhodopsin mutations, Medullary thyroid carcinoma, Cardiac atrial amyloidosis, Pituitary prolactinoma, Hereditary lattice corneal dystrophy, Cutaneous lichen amyloidosis, Mallory bodies, Corneal lactoferrin amyloidosis, Pulmonary alveolar proteinosis, Odontogenic (Pindborg) tumor amyloid, Seminal vesicle amyloid, Cystic Fibrosis, Sickle cell disease, or Critical illness myopathy. in certain embodiments, a cell accumulating misfolded proteins is a cell misfolding one or more proteins such as Amyloid β peptide (Aβ), Tau protein, Amyloid β peptide (Aβ), Amyloid β peptide (Aβ), Prion protein, α-Synuclein, Microtubule-associated protein tau (Tau protein), TDP-43, Fused in sarcoma (FUS) protein, Superoxide dismutase, TDP-43, FUS, Proteins with tandem glutamine expansions, ABri, ADan, Cystatin C, Notch3, Glial fibrillary acidic protein (GFAP), Seipin, Transthyretin, Serpins, Monoclonal immunoglobulin light chains, Immunoglobulin heavy chains, Amyloid A protein, Islet amyloid polypeptide (IAPP; amylin), Medin (lactadherin), Apolipoprotein AI, Apolipoprotein AII, Apolipoprotein AIV, Gelsolin, Lysozyme, Fibrinogen, Beta-2 microglobulin, Amyloid β peptide (Aβ), Crystallins, Rhodopsin, Calcitonin, Atrial natriuretic factor, Prolactin, Keratoepithelin, Keratins, Keratin intermediate filament proteins, Lactoferrin, Surfactant protein C (SP-C), Odontogenic ameloblast-associated protein, Semenogelin I, cystic fibrosis transmembrane conductance regulator (CFTR) protein, Hemoglobin, or Hyperproteolytic state of myosin ubiquitination.

The term "cell receptor" is not limited to any particular receptor. For example, it may be a G-protein coupled receptor, an ion channel or a cross-membrane transporter. Specific examples are CD3, CD4, CD8, CD28, CD16, and NKp46.

The cell signalling molecule may be a cytokine, such as a chemokine, an interferon, an interleukin, a lymphokine or a tumour necrosis factor, or a hormone or growth factor.

In one embodiment of the sixth aspect, the antibody or derivative thereof is multispecific, e.g. bispecific, and further binds to an effector molecule, e.g. a cytotoxic substance or a receptor ligand.

Further targets to which the dimer or the antibody or derivative of the sixth aspect can bind are the antigens described with respect to the second aspect above.

In another embodiment of the sixth aspect, the antibody or derivative thereof is multispecific, e.g. bispecific, and binds to said pathogen, diseased cell or cell signalling molecule with a further variable region.

All terms used with respect to the sixth aspect have the meanings as defined with respect to the first, second, third, fourth and fifth aspect, unless specifically defined otherwise. Further, all embodiments specified for the first, second, third, fourth and fifth aspect that are applicable to the sixth aspect are also envisaged for the sixth aspect.

A seventh aspect relates to a method of isolating the antibody or derivative thereof of the second aspect, comprising the steps of (i) providing a solution comprising a heavy chain A and a light chain A according to the first aspect and a heavy chain B and a light chain B as defined in the second aspect, (ii) purifying the antibody or derivative without a means for selecting for the pairing of heavy chain A with light chain A and/or the pairing of heavy chain B with light chain B.

In some embodiments, the solution may comprise
the antibody or derivative of the second aspect,
an antibody or derivative comprising two heavy chains A according to the first aspect, and
an antibody or derivative comprising two heavy chains B as defined in the second aspect.

In some embodiments, the solution does not comprise an antibody or derivative wherein light chain A is paired with heavy chain B and/or wherein light chain B is paired with heavy chain A.

In one embodiment, step (i) comprises expressing the one or more polynucleotides of the third aspect in a cell and optionally lysing the cell. The purifying of the antibody or derivative may include a means known in the art, for example physicochemical fractionation (e.g. differential precipitation, size-exclusion or solid-phase binding of immunoglobulins based on size, charge or other shared chemical characteristics of antibodies), class-specific affinity, or antigen-specific affinity.

In one embodiment, the antibody or derivative thereof is the antibody or derivative of the second aspect according to the "bivalent Fab configuration" or a symmetric antibody or derivative thereof of the second aspect (e.g. in the "tetravalent spider configuration") and the antibody or derivative is purified without a means for selecting for heavy chain pairing, e.g. a pairing of heavy chain A with heavy chain B.

In another embodiment, in which the heavy chains of the antibody or derivative thereof may comprise knob-into-hole mutations, the antibody or derivative thereof is the antibody or derivative of the second aspect has a Y-shaped IgG like form (including the "IgG configuration", the "TBTI configuration" and the "CODV configuration"), and the antibody or derivative is purified including a means for selecting for a pairing of heavy chain A with heavy chain B. For example, the means for selecting for a pairing of heavy chain A with heavy chain B includes selecting for Protein A binding (e.g. by Protein A chromatography), selecting for the presence of a $C_H1$ domain or a $C_L$ (or Cκ) domain (e.g. by Kappa Select chromatography), or for the absence of a CH2 domain, or selecting for Protein A binding (e.g. by Protein A chromatography), followed by selecting for the presence of a $C_H1$ domain or a $C_L$ (or Cκ) domain (e.g. by Kappa Select chromatography), or for the absence of a CH2 domain.

In another embodiment, wherein the Fc regions of heavy chain A and heavy chain B comprise knob-into-hole mutations and either the Fc region of heavy chain A or the Fc region of heavy chain B comprises one or more mutations abolishing the binding to Protein A, and wherein the heavy chain comprising the hole mutation (of the knob-into-hole mutations) comprises the one or more mutations abolishing the binding to Protein A, the method of the seventh aspect does not comprise selecting for the presence of a $C_H1$ domain or a $C_L$ (or Cκ) domain (e.g. by Kappa Select chromatography), or for the absence of a CH2 domain. The omission of this selection is possible since the knob-into-hole approach allows for dimerization also of two "hole" heavy chains, but not for dimerization of two "knob" heavy chains. Therefore, if the "hole" heavy chain has the one or more mutations decreasing, e.g. abolishing the binding to Protein A and it is selected with Protein A chromatography, one will select against the "hole" dimers and isolate only the bispecific antibody without any further steps.

All terms used with respect to the seventh aspect have the meanings as defined with respect to the first, second, third, fourth, fifth and sixth aspect, unless specifically defined otherwise. Further, all embodiments specified for the first, second, third, fourth, fifth and sixth aspect that are applicable to the seventh aspect are also envisaged for the seventh aspect.

Some exemplary antibodies (A-I) are represented by amino acid sequences as follows:

(A) A tetravalent spider antibody (see FIG. 1E) having
light chains A according to SEQ ID NO: 3, wherein residues 1-113 are the variable domain A and may be substituted with a variable domain having a different specificity than the one exemplified,
heavy chains according to SEQ ID NO: 4, wherein residues 1-120 are the variable domain A and may be substituted with a variable domain having a different specificity, and residues 239-358 are the variable domain B and may be substituted with a variable domain having a different specificity than the one exemplified, and
light chains B according to SEQ ID NO: 5, wherein residues 1-107 are the variable domain B and may be substituted with a variable domain having a different specificity than the one exemplified.

(B) A bispecific IgG1 antibody (see FIG. 1A) with MCH2 domains, having:
a light chain A according to SEQ ID NO: 6, wherein residues 1-112 are the variable domain A and may be substituted with a variable domain having a different specificity than the one exemplified,
a heavy chain A according to SEQ ID NO: 7, wherein residues 1-113 are the variable domain A and may be substituted with a variable domain having a different specificity than the one exemplified,
a light chain B according to SEQ ID NO: 8, wherein residues 1-107 are the variable domain B and may be substituted with a variable domain having a different specificity than the one exemplified, and
a heavy chain B according to SEQ ID NO: 9, wherein residues 1-118 are the variable domain B and may be substituted with a variable domain having a different specificity than the one exemplified.

(C) A bispecific IgG1 antibody (see FIG. 1A) with MCH2 domains, having:
a light chain A according to SEQ ID NO: 10, wherein residues 1-111 are the variable domain A and may be substituted with a variable domain having a different specificity than the one exemplified,
a heavy chain A according to SEQ ID NO: 11, wherein residues 1-118 are the variable domain A and may be substituted with a variable domain having a different specificity than the one exemplified,
a light chain B according to SEQ ID NO: 12, wherein residues 1-107 are the variable domain B and may be substituted with a variable domain having a different specificity than the one exemplified, and
a heavy chain B according to SEQ ID NO: 13, wherein residues 1-123 are the variable domain B and may be substituted with a variable domain having a different specificity than the one exemplified.

(D) A bivalent Fab (FIG. 1B) wherein $CH2_H$ is linked to $V_HB$ instead of $DIM_H$, having
a light chain A according to SEQ ID NO: 14, wherein residues 1-112 are the variable domain A and may be substituted with a variable domain having a different specificity than the one exemplified,
a heavy chain according to SEQ ID NO: 15, wherein residues 1-121 are the variable domain A and may be substituted with a variable domain having a different specificity, and wherein residues 240-359 are the variable domain B and may be substituted with a variable domain having a different specificity than the one exemplified, and
a light chain B according to SEQ ID NO: 16, wherein residues 1-113 are the variable domain A and may be substituted with a variable domain having a different specificity than the one exemplified.

(E) A bivalent bispecific antibody, wherein two variable domains B are each part of a heavy chain and these heavy chains HC1 and HC2 are paired with each other (thereby pairing the variable domains B), and wherein heavy chain HC1 is linked to an MCH2 domain linked to a variable domain A and the MCH2 domain pairs with a further MCH2 domain which is linked to a variable domain A to form a light chain LC1 (thereby pairing the variable domains A), having
a light chain LC1 according to SEQ ID NO: 17, wherein residues 1-112 are the variable domain A and may be substituted with a variable domain having a different specificity than the one exemplified,
a heavy chain HC1 according to SEQ ID NO: 18, wherein residues 1-121 are the variable domain A and may be substituted with a variable domain having a different specificity, and wherein residues 240-359 are the variable domain B and may be substituted with a variable domain having a different specificity than the one exemplified, and
a light chain LC2 according to SEQ ID NO: 19, wherein residues 1-113 are the variable domain B and may be substituted with a variable domain having a different specificity than the one exemplified.

(F) A CH2E-pseudo-CODV antibody (see FIG. 7A) having
a chain 1 according to SEQ ID NO: 20, wherein residues 1-118 are the variable domain 1 and residues 120-242 are the variable domain 2 (both may be substituted with a variable domain having a different specificity than the one exemplified), and
a chain 2 according to SEQ ID NO: 21, wherein residues 1-107 are the variable domain 2 and residues 115-225 are the variable domain 1 (both may be substituted with a variable domain having a different specificity than the one exemplified).

(G) A pseudo hinge-CH2E-hybrid-Fab2 (see FIG. 8A) having
a heavy chain A according to SEQ ID NO: 22, wherein residues 1-123 are the variable domain A and may be substituted with a variable domain having a different specificity than the one exemplified,
a light chain A according to SEQ ID NO: 23, wherein residues 1-106 are the variable domain A and may be substituted with a variable domain having a different specificity than the one exemplified,
a heavy chain B according to SEQ ID NO: 24, wherein residues 1-118 are the variable domain B and may be substituted with a variable domain having a different specificity than the one exemplified,
a light chain B according to SEQ ID NO: 25, wherein residues 1-111 are the variable domain B and may be substituted with a variable domain having a different specificity than the one exemplified, (H) A bispecific IgG1 antibody (see FIG. 1A) with ECH2 domains, having:
- a light chain A according to SEQ ID NO: 26, wherein residues 1-110 are the variable domain A and may be substituted with a variable domain having a different specificity than the one exemplified,
- a heavy chain A according to SEQ ID NO: 27, wherein residues 1-123 are the variable domain A and may be substituted with a variable domain having a different specificity than the one exemplified,
- a light chain B according to SEQ ID NO: 28, wherein residues 1-111 are the variable domain B and may be substituted with a variable domain having a different specificity than the one exemplified, and
- a heavy chain B according to SEQ ID NO: 29, wherein residues 1-118 are the variable domain B and may be substituted with a variable domain having a different specificity than the one exemplified.

(I) A trivalent antibody (see FIG. 1F) with MCH2 domains, having:
- a light chain A according to SEQ ID NO: 30, wherein residues 1-111 are the variable domain A and may be substituted with a variable domain having a different specificity than the one exemplified (anti-IL13-(huzdBB13)-VL-huMCH2),
- a heavy chain A according to SEQ ID NO: 31, wherein residues 1-118 are the variable domain A and may be substituted with a variable domain having a different specificity than the one exemplified (anti-IL13-(huzdBB13)-VH-huMCH2-huIgG1-Fc (hole-RF)),
- a light chain B according to SEQ ID NO: 32, wherein residues 118-224 are the variable domain B and residues 1-107 are the variable domain Y, and both may be substituted with variable domains having a different specificity than the ones exemplified (CODV-anti-IL4-(huzd8D4-8)-VL-anti-TNFalpha-(Adalimumab)-VL-huIGLC2), and
- a heavy chain B according to SEQ ID NO: 33, wherein residues 1-121 are the variable domain B and residues 122-244 are the variable domain Y, and both may be substituted with variable domains having a different specificity than the ones exemplified (CODV-anti-TNFalpha-(Adalimumab)-VH-anti-IL4-(huzd8D4-8)-VH-huIGHG1(knob)). This antibody is trispecific, but variable domains can be substituted also in a way making the antibody bispecific or monospecific.

Instead of the above chains, variants thereof may be used. A variant has an amino acid sequence that is at least 80%, 85%, 90%, 95%, 96%, 97%, 98% or 99% identical to the amino acid sequence it is derived from, for example identical to a sequence selected from the group consisting of SEQ ID NO: 3 to 33. The determination of percent identity between two sequences is accomplished as described above. Also, in all the above examples, the MCH2/ECH2 domains can be swapped with the $DIM/C_H1C_k$ domains, as applicable.

In the following figures and examples, some embodiments are described in more detail. Yet, no limitation of the invention is intended by the details of these embodiments. In contrast, the invention pertains to any embodiment which comprises details which are not explicitly mentioned in the embodiments herein, but which the skilled person finds without undue effort.

DESCRIPTION OF THE EXAMPLES

Material & Methods

Generation of Expression Plasmids

Figure 1:
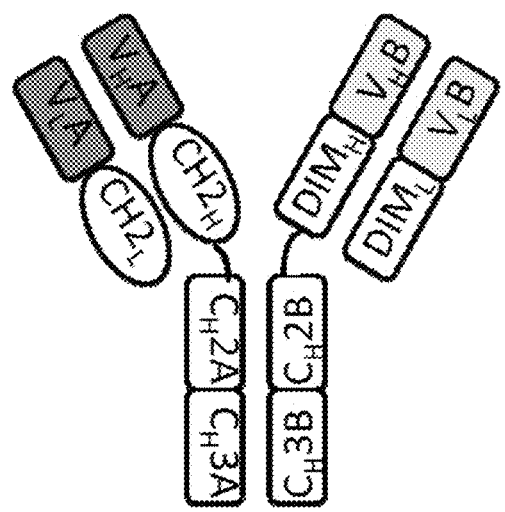
FIG. 1: Examples of antibody or derivative configurations. Different dimerization domains ensure correct pairing of the variable domains. A: IgG configuration (linkers not shown except Fc-Fab linking by the hinge region), B: Bivalent Fab configuration (linkers not shown except Fab-Fab linker; this linker may alternatively link $CH2_H$ with $DIM_L$, $CH2_L$ with $DIM_H$ or $CH2_L$ with $DIM_L$), C: TBTI configuration (linkers not shown except Fc-Fab linking by the hinge region), D: CODV configuration showing two possible linker configurations on the left and on the right arm (both arms can also have the same linker configuration, i.e. that of the left or of the right arm shown), E: Tetravalent spider configuration (linkers not shown except Fc-Fab linking by the hinge region and Fab-Fab linkers), F: trivalent configuration (example for the CODV chimera configuration) containing three binding sites allowing for mono-, bi- and tri-specificity. The right arm shown is a CODV arm having the linker configuration of the right arm of the CODV configuration of FIG. 1 D, but it may instead also have the linker configuration of this CODV configuration. The left arm is a conventional IgG arm. Left and right arms are exchangeable, i.e. the left arm can be the CODV arm and the right arm the IgG arm. Further, the MCH2 domains are shown to be in the IgG arm, but they can instead be in the CODV arm (independent of its linker configuration) with the DIM domains then being in the IgG arm.
Figure 1:
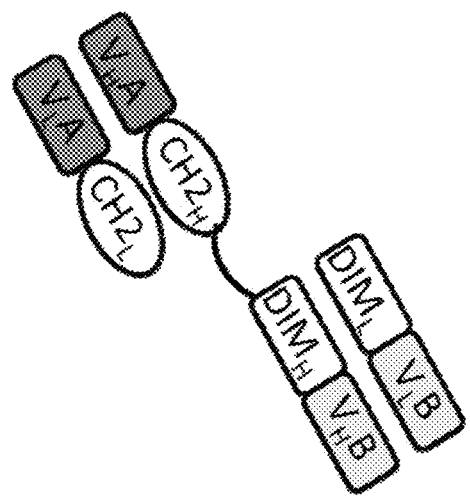
Figure 1:
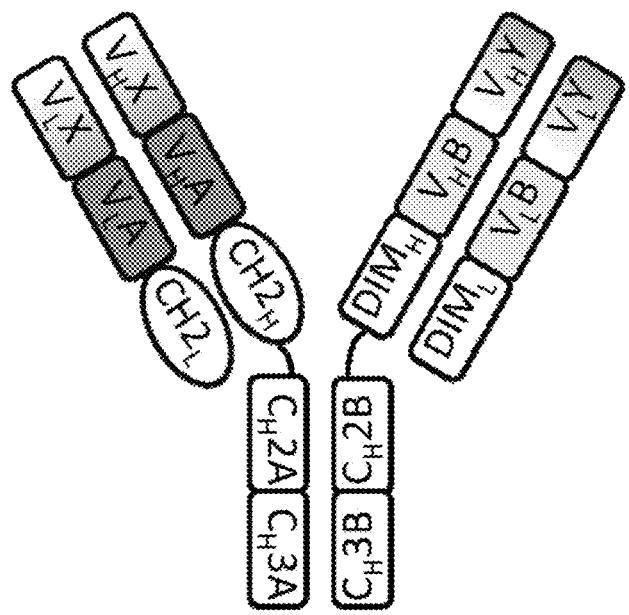
Figure 1:
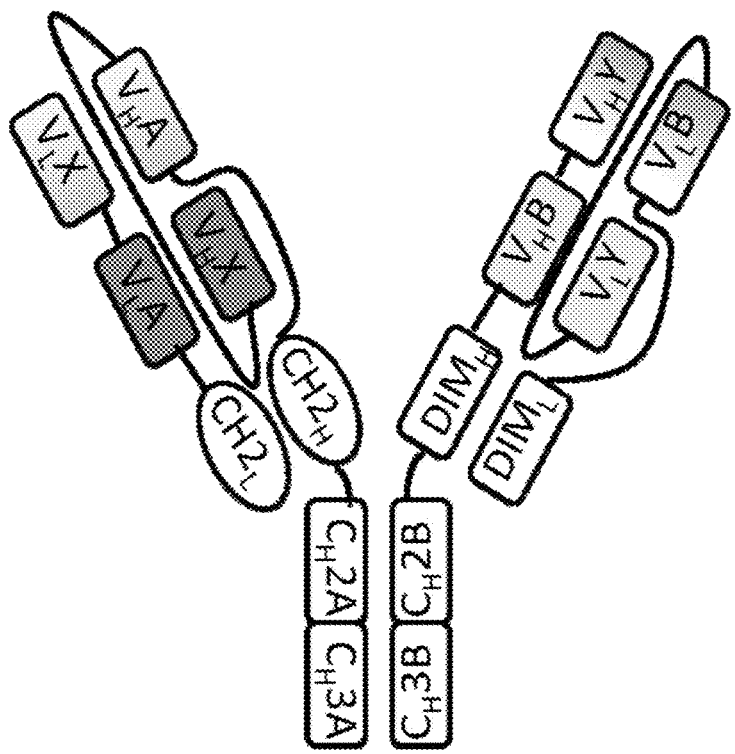
Figure 1:
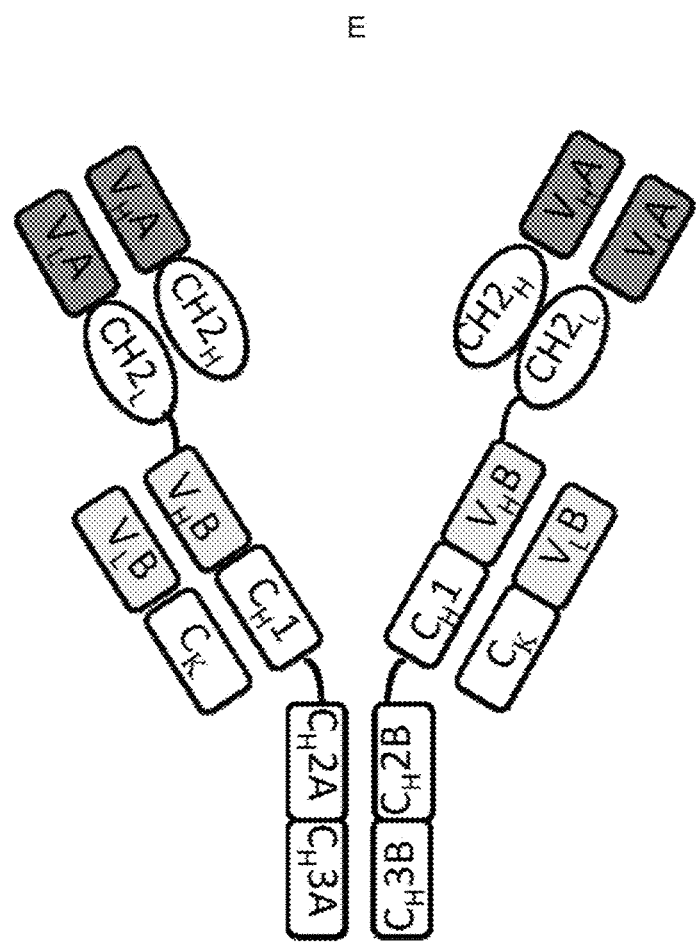
Figure 1:
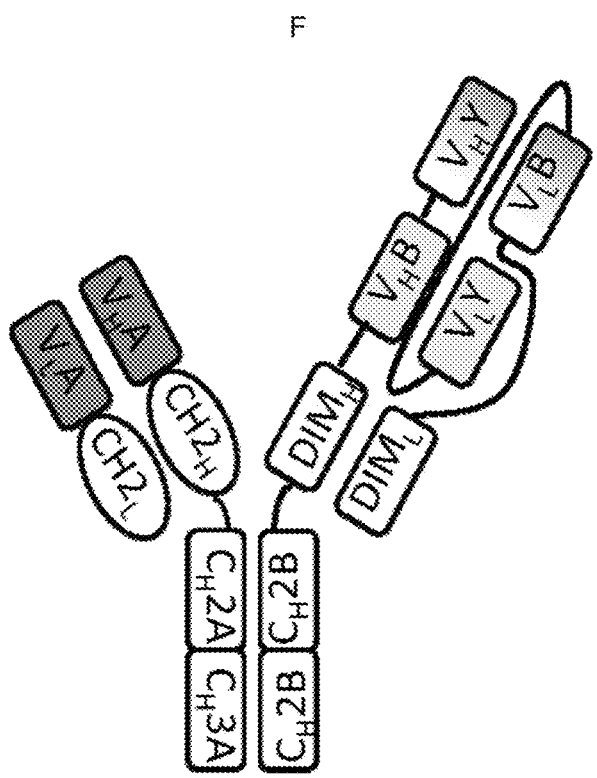

All described constructs were built from gene synthesis fragments (GENEART), cleaved with restriction enzymes and ligated into mammalian expression vector pXL. The vector was used to transform E. coli and clones were selected and amplified to isolate DNA for transient transfection using Qiagen Kits. The DNA sequence was verified by sequencing of the relevant ORF and sequence context. The resulting coding ORFs are in accordance with the before listed and described sequences.

Expression of Recombinant Proteins

All protein production campaigns were realized via transient expression. Freestyle HEK293 (Life) cells growing in F17 serum free suspension culture (Life) were transfected with the expression plasmid. Transfections were performed using Cellfectin transfection reagent (Life). The cells were cultured at 37° C. for 7 days at 8% $CO_2$ in shaker flasks. The culture supernatant containing recombinant protein was harvested by centrifugation and was clarified by filtration (0.22 µm). Recombinant IgG1 constructs were purified by affinity chromatography on Protein A (HITRAP Protein A HP Columns, GE Life Sciences). After elution from the column with 100 mM acetate buffer and 10 mM NaCl, pH 3.5, the CODV-IgG1 constructs were desalted using HiPrep 26/10 Desalting Columns, formulated in PBS at a concentration of 1 mg/mL and filtered using a 0.22 µm membrane. Fab-like constructs were purified by IMAC on HITRAP, IMAC HP Columns (GE Life Sciences). After elution from the column with a linear gradient (Elution buffer: 20 mM sodium phosphate, 0.5 M NaCl, 50-500 mM imidazole, pH 7.4), the protein containing fractions were pooled and desalted using HiPrep 26/10 Desalting Columns, formulated in PBS at a concentration of 1 mg/mL and filtered using a 0.22 µm membrane. For purification of asymmetric heterodimeric constructs the protein samples were additionally applied on His-Trap column (GE) and/or captured by Kappa select (GE) after capture on protein A and desalting step. The protein was polished by SEC using a SUPERDEX 200 (GE). After a final ultrafiltration concentration step the protein was used for different assays. This strategy was used to isolate heterodimers from homodimers. Protein concentration was determined by measurement of absorbance at 280 nm. Each batch was analyzed by SDS-PAGE under reducing and non-reducing conditions to determine the purity and molecular weight of each subunit and of the monomer.

Characterization of MCH2 and ECH2 Variants

To determine whether the MCH2 and ECH2 antibody-like protein heavy and light chains were pairing and folding properly, the aggregation level was measured by analytical size-exclusion chromatography (SEC). Analytical SEC was performed on assembled pairs using an ÄKTA EXPLORER 10 (GE Healthcare) equipped with a TSKgel G3000SWXL column (7.8 mm×30 cm) and TSKgel SWXL guard column (Tosoh Bioscience). The analysis was run at 1 ml/min. using 250 mM NaCl, 100 mM Na-phosphate, pH 6.7, with detection at 280 nm. 30 µl of protein sample (at 0.5-1 mg/ml) were applied onto the column. For estimation of the molecular size, the column was calibrated using a gel filtration standard mixture (MWGF-1000, SIGMA Aldrich). Data evaluation was performed using UNICORN software v5.11.

Binding Analysis by SPR

Two pairs of heavy and light chains were selected for full kinetic analysis. Recombinant human IL13 and IL4 was purchased from Chemicon (USA). Kinetic characterization of purified antibodies was performed using surface plasmon resonance technology on a BIACORE 3000 (GE Healthcare). A capture assay using a species-specific antibody (e.g., human-Fc specific MAB 1302, Chemicon) for capture and orientation of the investigated antibodies was used. The capture antibody was immobilized via primary amine groups (11000 RU) on a research grade CM5 chip (GE Life Sciences) using standard procedures. The analyzed antibody was captured at a flow rate of 10 µL/min with an adjusted RU value that would result in maximal analyte binding of 30 RU. Binding kinetics were measured against recombinant human IL4 and IL13 over a concentration range between 0 to 25 nM in HBS EP (10 mM HEPES, pH 7.4, 150 mM NaCl, 3 mM EDTA, and 0.005% Surfactant P20) at a flow rate of 30 µl/min. Chip surfaces were regenerated with 10 mM glycine, pH 2.5. Kinetic parameters were analyzed and calculated in the BIAevaluation program package v4.1 using a flow cell without captured antibody as reference.

"Redirected" Cell Killing

Peripheral blood mononuclear cells (PBMCs) were isolated from 200 ml peripheral blood of healthy donors treated with EDTA by Ficoll density centrifugation. 15 ml Histopaque (Sigma-Aldrich) was preloaded on a 50 ml Leucosep-Tube (Greiner bio-one). Blood was diluted with autoMACS Rinsing Buffer+1% BSA (Miltenyi Biotec) and loaded on the membrane of a total of ten prepared tubes. Tubes were centrifuged without brake for 10 min at 1000 xg. PBMCs were collected and washed with autoMACS Rinsing Buffer+1% BSA three times. Finally, PBMCs were resuspended in autoMACS Running Buffer (Miltenyi Biotec) for isolation of T lymphocytes by autoMACSpro technology using the Pan T Cell isolation Kit (Miltenyi Biotec) according to manufacturer's instructions. Purity of separated T cells was analyzed by MACSQuant flow cytometry using the human 7-Color Immunophenotyping Kit (Miltenyi Biotec). T-cell engaging effect of bispecific antibodies was analyzed by a flow cytometry based cytotoxic assay. Target cells (i.e. THP-1 cell line) were stained for 15 min at 37° C. with 1 µM CFSE in 1 ml RPMI+GlutaMAX I (Gibco) per 1E7 cells. Afterwards, cells were washed twice and resuspended in RPMI+GlutaMAX I+10% FCS (Invitrogen). 2.5E4 target cells were seeded in 96-well U-bottom suspension culture plates (Greiner bio-one) in 50 µl medium per well. Isolated primary human T lymphocytes were resuspended in RPMI+GlutaMAX I+10% FCS and were added at indicated effector-to-target ratio in 50 µl per well to the target cells (e.g. E:T=10:1). Bispecific antibodies were diluted 1:3 in serial in PBS (Invitrogen) and 5 µl each were added to the cells at a final maximum concentration of 3000 ng/ml. The assay was incubated for 20 h at 37° C. in 5% CO2. To detect dead target cells, all cells were stained with 7-AAD. Therefore, 5 µg/ml 7-AAD diluted in Stain Buffer with FBS (BD Pharmingen) were added to each well and were incubated for 15 min at 4° C. in the dark. Cells were measured using the MACSQuant (Miltenyi Biotec) or LSRII (BD) flow cytometer, respectively. Further data analyses were performed using the FlowJo software (Tree Star, Inc.). Read out was percentage of CFSE and 7-AAD double positive cells. The results of these investigations demonstrate the ability of the CD123xCD3 Fabs to mediate redirected killing of tumor cells.

Example 1: IgG Configuration ($MC_H2$), RF Mutations

Figure 2:
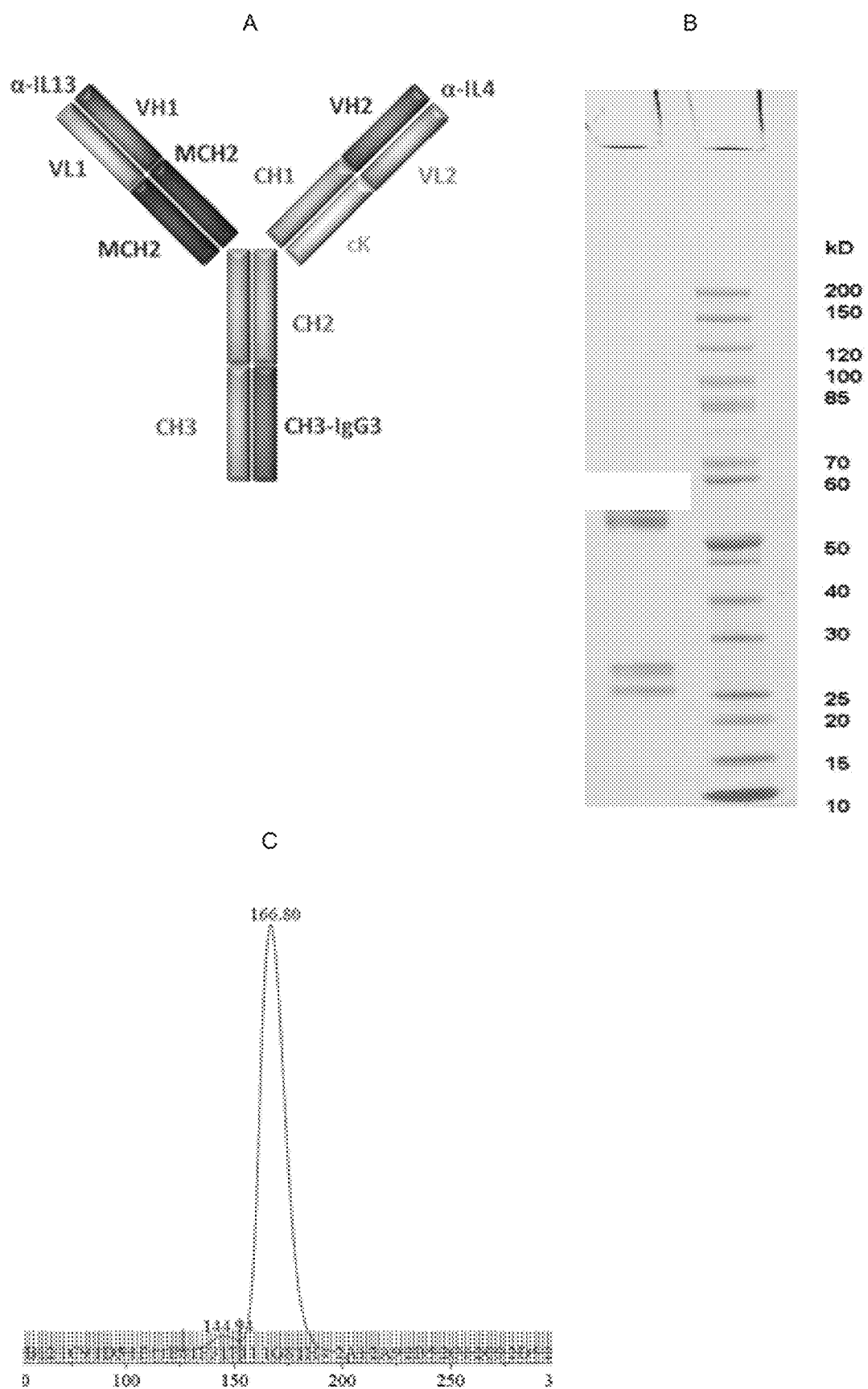
FIG. 2: Schematic representation of the architecture of the asymmetric antibody. A: On one half of the antibody like structure the CH1/kappa region is replaced by the MCH2 domains. The Fc of the Fab containing half is chimeric, harbouring the CH3 from IgG3 whereas all other Fc domains are of IgG1 origin. A two step purification including protein A and kappa select chromatography allows the isolation of the correct assembled heterodimeric molecule. B: SDS-PAGE showing the chain composition under reducing conditions. C: SEC profile of the purified heterodimeric antibody.

As described in the Material & Methods section, an antibody in the IgG configuration comprising an IgG3-CH3 domain in one Fc chain and an IgG1-CH3 domain in the other and variable domains being IL13 and IL4 was generated, wherein the $CH2_H$ and $CH2_L$ domains are an IgM constant domain $MC_H2$ (see FIG. 2A). It was purified with the following steps:
1. Protein A chromatography
2. Kappa select chromatograpy
3. Desalting on HiPrep 26/10

The yield was 4 mg/l. SDS-PAGE on NuPAGE® Novex® 4-12% Bis-Tris (FIG. 2B) showed the expected number and size of fragments under reducing conditions. SEC analysis of the purified protein showed a monomer level of 96% (FIG. 2C). Biacore analysis showed binding to the corresponding antigens and binding kinetics as expected from the parental antibodies (Table 2).

TABLE 2

| Binding kinetics of the purified bispecific antibody against IL4 and IL13 | | | |
| --- | --- | --- | --- |
| Analyte | ka (1/Ms) | Kd (1/s) | KD (M) |
| IL13 | 1.49E+06 | 8.21E−05 | 5.50E−11 |
| IL4 | 1.51E+08 | 2.53E−04 | 1.68E−12 |

Example 2: IgG Configuration ($MC_H2$), RF and Knob-into-Hole Mutations

Figure 3:
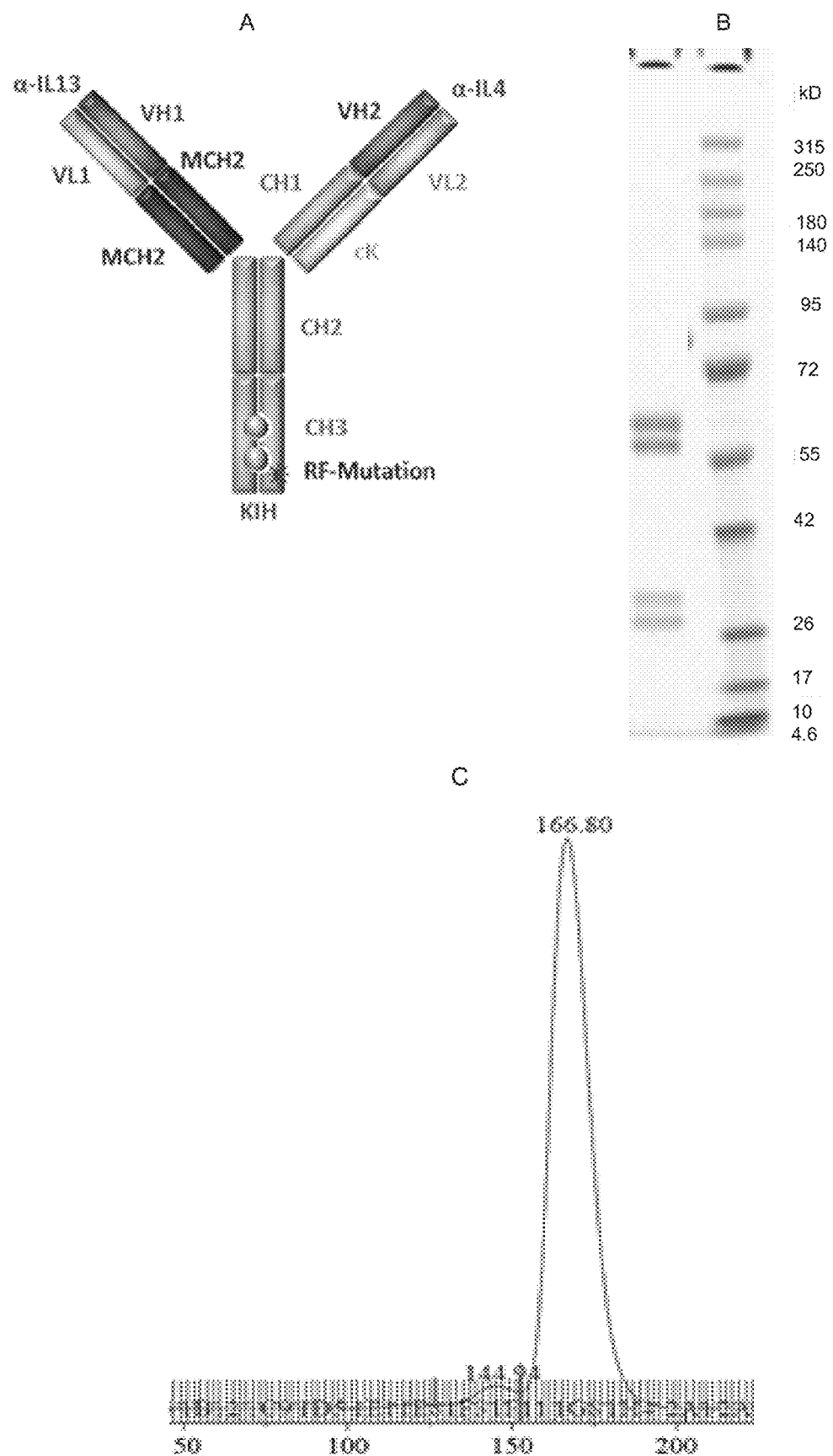
FIG. 3: Schematic representation of the architecture of the asymmetric antibody. A: On one half of the antibody like structure the CH1/kappa region is replaced by the MCH2 domains. The heterodimerization is driven by knobs-into-holes mutations within the Fc parts. The Fc part with the hole mutations further contains the RF mutation. A two-step purification including protein A and kappa select chromatography allows the isolation of the correct assembled heterodimeric molecule. B: SDS-PAGE showing the chain composition under reducing conditions. C: SEC profile of the purified heterodimeric antibody.

As described in the Material & Methods section, an antibody in the IgG configuration comprising mutations H435R and Y436F (RF mutations) in one CH3 domain as well as know-into-hole mutations and variable domains binding IL13 and IL4 was generated (see FIG. 3A). It was purified with the following steps:
1. Protein A chromatography
2. Kappa select chromatograpy
3. Desalting on HiPrep 26/10

The yield was with 10 mg/l more than double as high as for the variant described in example 1, indicating a higher efficiency of correct chain association driven by the knob-into-hole modification of the Fc fragments. SDS-PAGE on NuPAGE® Novex® 4-12% Bis-Tris (FIG. 3B) showed under reducing conditions the expected number and size of fragments SEC analysis of the purified protein showed a monomer level of 96% (FIG. 3C). Biacore analysis showed binding to the corresponding antigens and binding kinetics as expected from the parental antibodies.

Example 3: Tetravalent Spider Configuration

As described in the Material & Methods section, an antibody in the Tetravalent spider configuration (see FIG. 4A) was generated. It was purified with the following steps:
1. Protein A chromatography
2. Desalting on HiPrep 26/10

Figure 4:
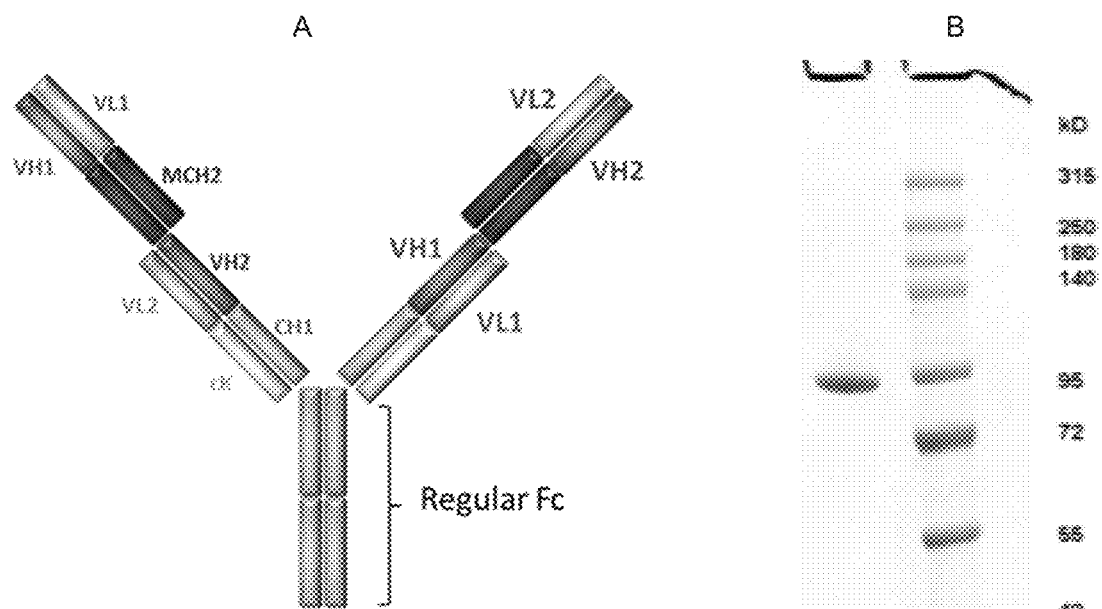
FIG. 4: Tetravalent spider configuration. A: Schematic representation of the symmetric IgG like structure. A single step protein A chromatography allows the isolation of the correctly assembled homodimeric molecule. B: SDS-PAGE showing the chain composition under reducing conditions. C: SEC profile of the purified heterodimeric antibody. D and E: Biacore sensograms showing binding to the corresponding antigens.
Figure 4:
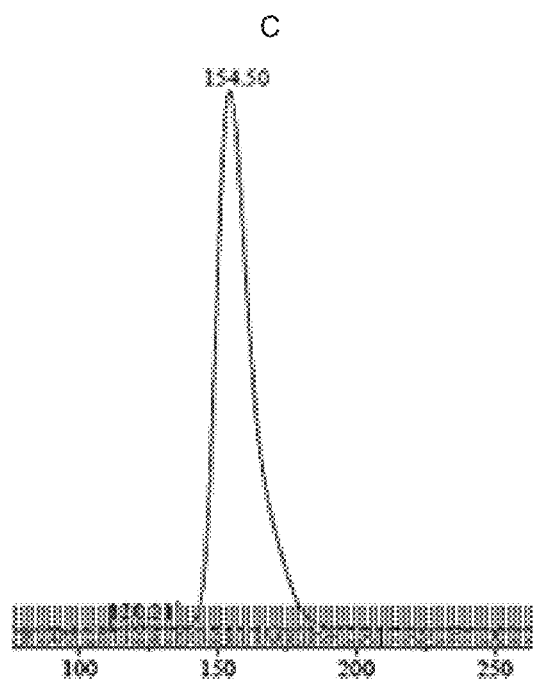
Figure 4:
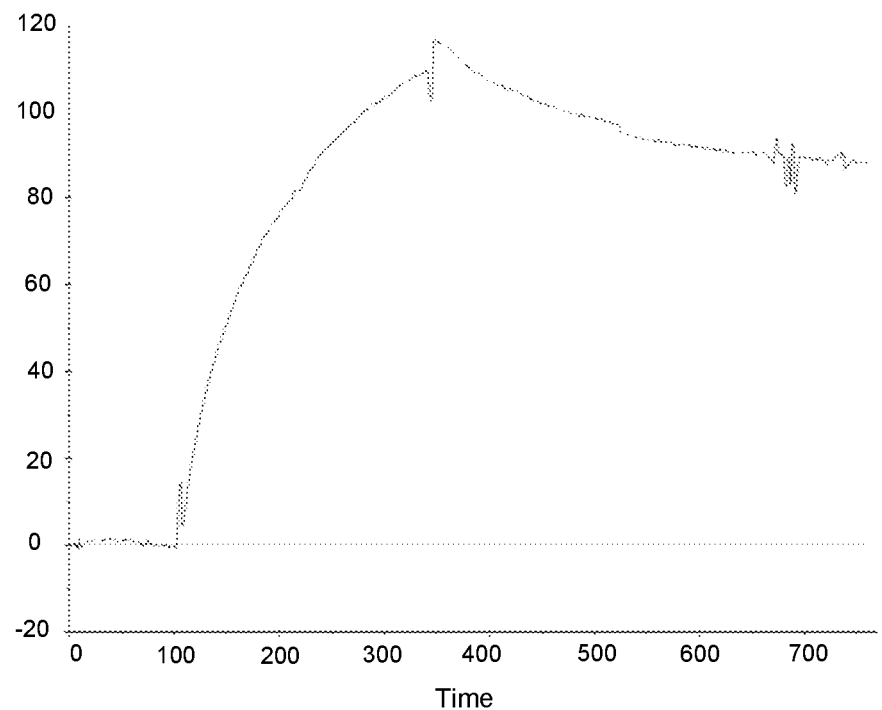
Figure 4:
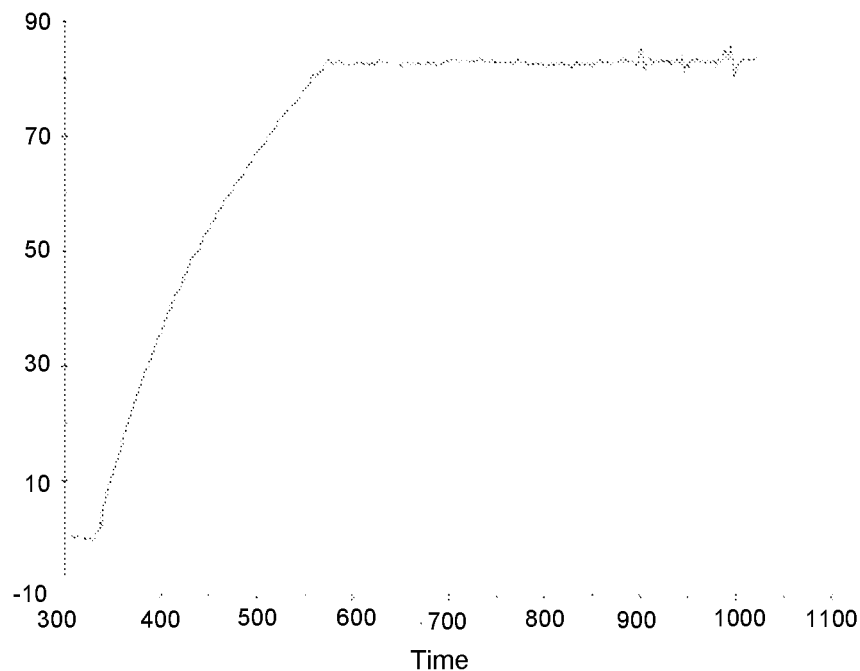

The yield was 5 mg/l. SDS-PAGE on NuPAGE® Novex® 4-12% Bis-Tris (FIG. 4B) showed all expected fragments with the expected size under non-reducing conditions. SEC analysis showed a monomer level of 98% (FIG. 4C). Biacore analysis (FIGS. 4D and E) showed binding against the corresponding antigens.

Example 4: IgG Configuration ($EC_H2$), RF and Knob-into-Hole Mutations

This bivalent bispecific antibody (see FIG. 5A) contains a CH2 domain of human IgE (Uniprot P01854) from amino acid position 104 to 210. The domain contains mutation of cysteine 105 to alanine to avoid unwanted cys reactivity and mutation of asparagine 146 to glutamine to avoid glycosylation. In the following examples called "CH2E". To fuse the CH2E part to the HC of the construct, a flexible linker (GSGSGS) was introduced.

Example using variable domains "huBB13" and "hu8D4-8" recognizing antigens: IL4 and IL13 described before (US 20100226923 A1) composed in an IgG like structure consisting of two different Fabs each representing a different target VD fused to a modified IgG1-Fc domain. To enhance the expression and formation of heterodimers KIH (knob into hole) mutations were introduced into the CH3 domains. L234A, L235A mutations (Hezareh et al. 2001, J. Virol., 75: 12161) were incorporated to prevent effector function of the Fc backbone. The ECH2 domain is replacing CH1/kappa.

The antibody comprises the chains
anti-IL4(hu8D4-8-VL1)-CL1gk
anti-IL4(hu8D4-8-VH1)-CH1g-Fc(IgG1 LALA knob RF)
anti-IL13-VL(huBB13-VL3)-CH2e
anti-IL13-(huBB13-VH2)-CH2e-Fc(IgG1 LALA hole)

A two-step affinity chromatography was performed to ensure enrichment of heterodimeric chain pairs. The protein was captured by HiTrap Protein A 5 ml (GE Healthcare) and eluted by pH shift. Protein fractions were collected and buffer was instantly exchanged to PBS by a HiPrep 26/10 Desalting 53 ml desalting column (GE Healthcare). The protein solution was applied to HiTrap KappaSelect 5 ml (GE Healthcare) and eluted via pH shift. Protein containing fractions were collected and buffer was instantly exchanged to PBS by a HiPrep 26/10 Desalting 53 ml desalting column (GE Healthcare). Fractions were pooled and sample volume was reduced via ultrafiltration. The protein was polished by SEC using a Superdex 200 (GE Healthcare) column. After a final ultrafiltration and 0.22 µm filtration step the protein solution was used for further assays.

Figure 5:
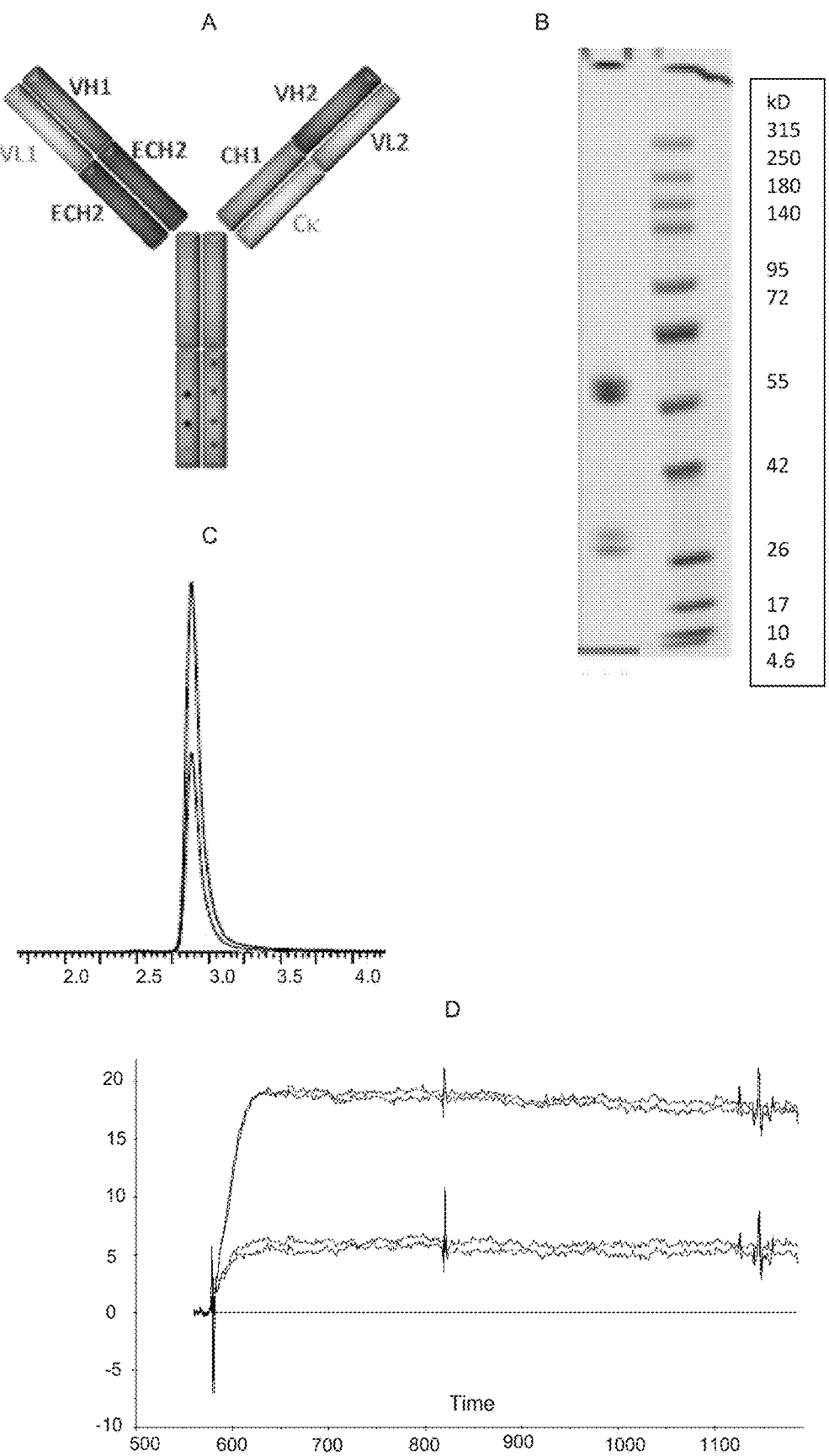
FIG. 5: Schematic representation of the architecture of the asymmetric antibody. A: On one half of the antibody like structure the CH1/kappa region is replaced by the ECH2 domains. The heterodimerization is driven by knobs-into-holes mutations within the Fc parts. The Fc part with the knob mutations further contains the RF mutation. B: SDS-PAGE showing the chain composition under reducing conditions. C: SEC profile of the purified protein. D: Biacore sensograms showing binding to IL4 and IL13.

The yield after purification was 18 mg/l. SDS-PAGE on NuPAGE® Novex® 4-12% Bis-Tris (FIG. 5B) showed the expected number and size of fragments under reducing conditions. SEC analysis of the purified protein showed a monomer level of ~99% (FIG. 5C). Biacore analysis showed binding to the corresponding antigens IL4 and IL13 (FIG. 5D).

Example 5: Bivalent Fab Configuration

Figure 6:
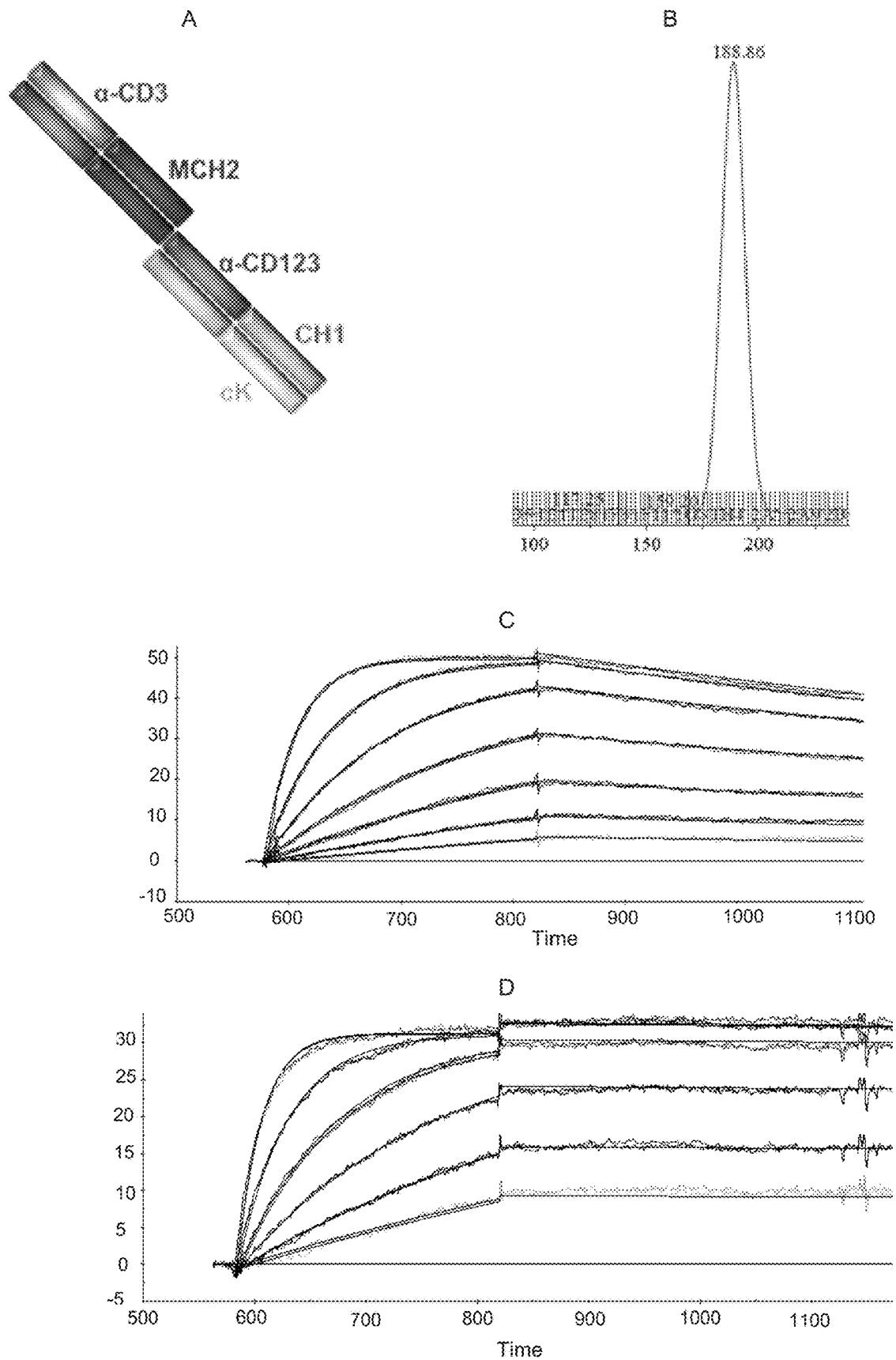
FIG. 6: Bivalent Fab configuration. A: schematic representation of the bivalent bispecific Fab fragment. B: SEC profile of the purified protein. C and D: Biacore sensograms showing binding to CD3 and CD123 respectively.

As described in the Material & Methods section, an antibody in Bivalent Fab configuration was generated, wherein the two Fabs are linked via a linkage of a MCH2 domain of one Fab-like fragment (CD3) to a variable domain of the other Fab (CD123), see FIG. 6A. The yield was 7 mg/l. SEC analysis showed a monomer level of 97% (FIG. 6B). Biacore analysis showed binding to the corresponding antigens (FIGS. 6C and D) and binding kinetics as expected from the parental antibodies (Table 3)

TABLE 3

Binding kinetics of the prurified bispecific bivalent Fab against CD3 and CD123

| Analyte | ka (1/Ms) | Kd (1/s) | KD (M) |
|---|---|---|---|
| CD123 | 4.5E+05 | 3.77E−05 | 8.38E−11 |
| CD3 | 1.581E+05 | 9.00E−04 | 5.71E−09 |

Example 6: CODV Bivalent Fab Configuration ($EC_H2$)

The bispecific F-like fragment (see FIG. 7A) contains a CH2 domain of human IgE (Uniprot P01854) from amino acid position 104 to 210. The domain contains mutation of cysteine 105 to alanine to avoid unwanted cys reactivity and mutation of asparagine 146 to glutamine to avoid glycosylation. In the example, variable domains "huBB13" and "hu8D4-8" are used recognizing antigens IL4 and IL13 described before (US 20100226923 A1). The molecule is composed in the CODV format. In this example, the ECH2 domain is replacing the CH1 and CL domains in some embodiments located at the C-terminal end of both chains to connect HC and LC via disulfide bridges. An 8x histidine tag was added for purification.

The antibody comprises 2 unique chains:

Chain 1: anti-IL13(huBB13-VH2)-anti-IL4(hu8D4-8-VH1)-ECH2-His

Chain 2: anti-IL4(hu8D4-8-VL1)-anti-IL13(huBB13-VL2)-ECH2

Figure 7:
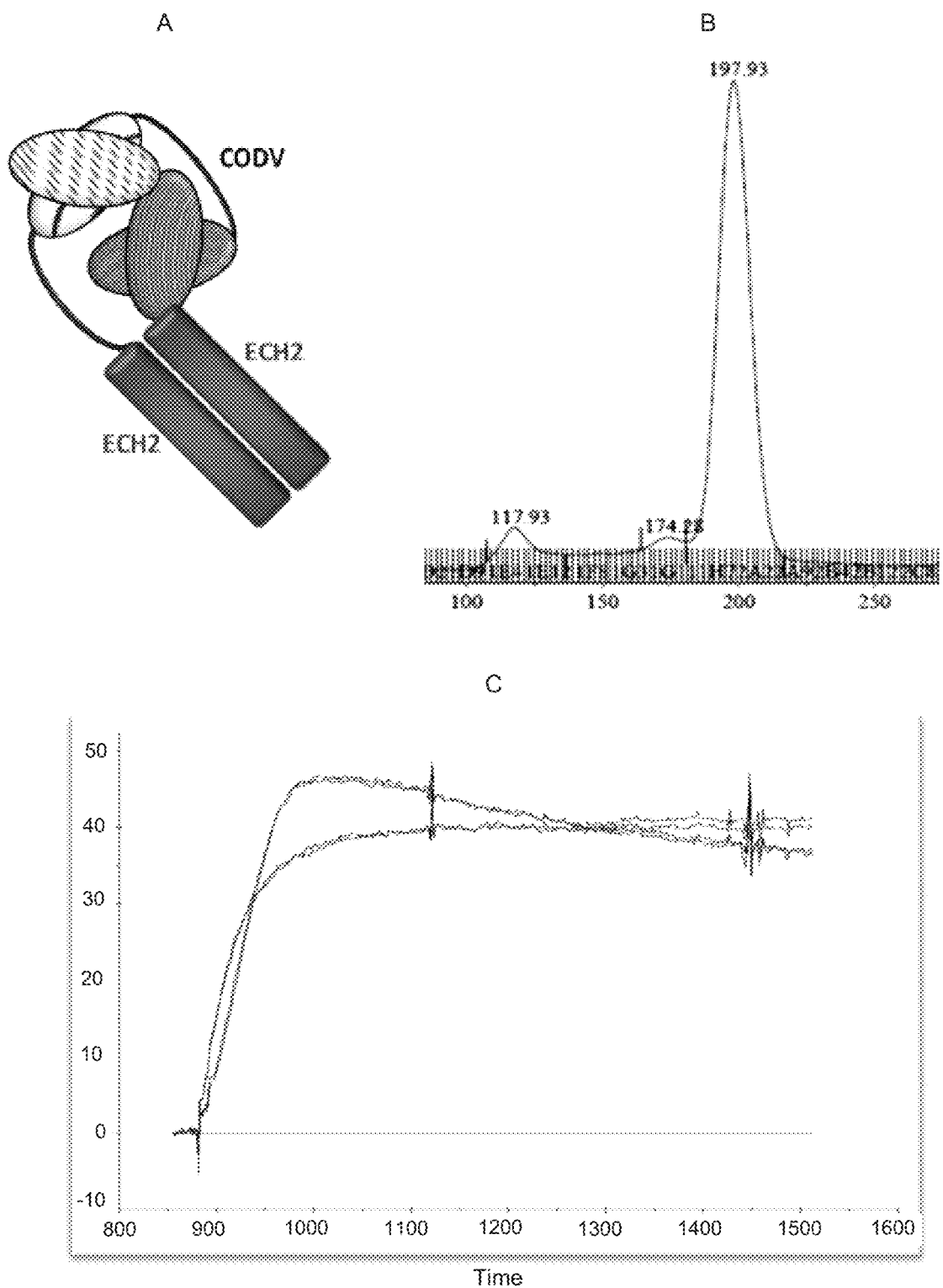
FIG. 7: CODV bivalent Fab configuration ($EC_H2$). A: schematic representation of the protein architecture. B: SEC profile of the purified protein. C: Biacore sensograms showing binding to both IL4 and IL13.

The His-tagged protein was captured on HisTrap High Performance 5 ml (GE Healthcare) and eluted by an imidazole gradient. The protein was polished by SEC using a Superdex 200 (GE Healthcare) By a final ultrafiltration concentration step the protein was concentrated and used for further assays. FIG. 7B shows the SEC profile of the Fab-like fragment after purification. Biacore analysis showed binding of both IL4 and IL13 (FIG. 7C).

Example 7: F(Ab')2 Like Configuration ($EC_H2$ Replacing the Hinge Region)

This F(ab')2-like antibody (see FIG. 8A) contains a CH2 domain of human IgE (Uniprot P01854) from amino acid position 104 to 210. The domain contains mutation of cysteine 105 to alanine to avoid unwanted cys reactivity and mutation of asparagine 146 to glutamine to avoid glycosylation. Also in this example, an inclusion of flexible linker connecting the CH2E domain on the heavy chain was introduced. Example using variable domains "huBB13" and "hu8D4-8" recognizing antigens IL4 and IL13 described before (US 20100226923 A1) composed in a $Fab_2$ like format. In this example, the ECH2 domain is replacing the hinge region to connect two Fab modules via HC parts. Generation of a bispecific molecule is done via heterodimerization of two different Fabs representing two separate target specifities. One Fab arm contains a MCH2 domain the other corresponds to a native Fab structure. In this example, anti-IL4 VD is connected to a CH1/kappa domain and the anti-IL13 VD is fused to a modified MCH2 domain. An 8x histidine tag was added at the Cter of one ECH2 domain for purification. The antibody comprises 4 unique chains:

anti-IL4 (hu8D4-8-VH1)-CH1g-CH2e
anti-IL4 (hu8D4-8-VL1)-Ck
anti-IL13 (huBB13-VH2)-MCH2-ECH2-8xHis
anti-IL13 (huBB13-VL3)-MCH2

Figure 8:
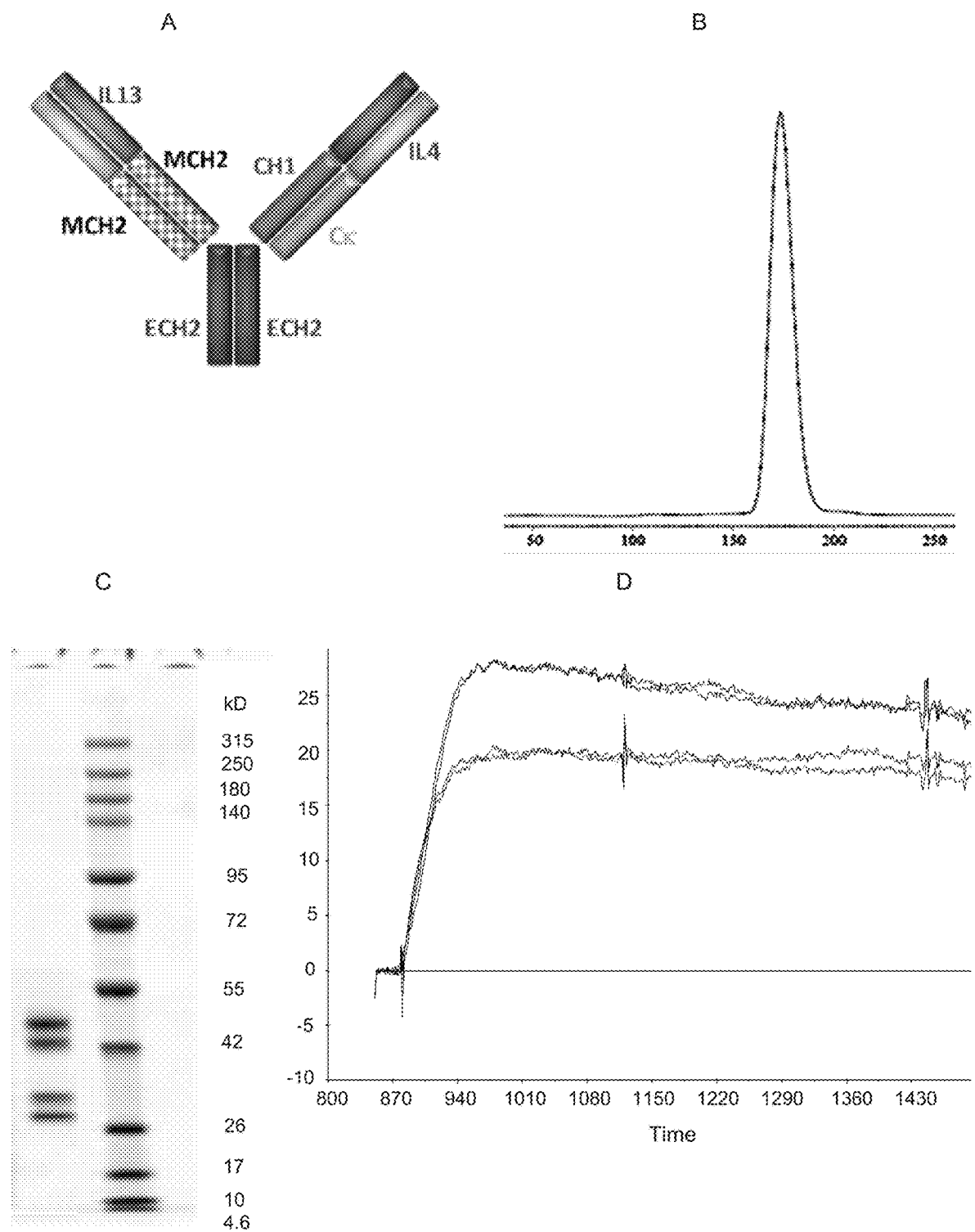
FIG. 8: F(ab')2 like configuration. A: schematic representation of the bivalent bispecific F(ab')2 like fragment. B: SEC profile of the purified heterodimeric antibody. C: SDS-PAGE showing the chain composition under reducing conditions. D: Biacore sensograms showing binding to IL4 and IL13.

A two-step affinity chromatography was performed to ensure enrichment of heterodimeric chain pairs. The protein was captured by HiTrap KappaSelect 5 ml (GE Healthcare) and eluted following manufacturer's instructions by pH shift. By a desalting column the buffer was immediately exchanged to PBS. After the protein solution was applied to HisTrap High Performance 5 ml (GE Healthcare) and eluted by an imidazole gradient. Afterwards the protein containing fractions were pooled and further polished by SEC using a Superdex 200 (GE Healthcare). After a final ultrafiltration concentration step the protein was used for further assays. The SEC profile after purification revealed a monomeric fraction of ~99% (FIG. 8B). A reducing SDS PAGE (Novex 4-12% Bis-Tris) showed the expected 4 fragment sizes (FIG. 8C). The construct is able to bind both IL4 and IL13 as demonstrated in Biacore analysis (FIG. 8D).

---

The invention claimed is:

1. An antibody or antigen-binding fragment thereof, comprising:
   (a) a heavy chain A and a light chain A, wherein the heavy chain comprises a variable domain $V_HA$ linked to a dimerization domain $CH2_H$ and the light chain comprises a variable domain $V_LA$ linked to a dimerization domain $CH2_L$, wherein both $CH2_H$ and $CH2_L$ are an IgM constant domain $MC_H2$ having the amino acid sequence of SEQ ID NO: 1, wherein $CH2_H$ and $CH2_L$ form a dimer, and wherein $V_HA$ and $V_LA$ form a first paratope AA, and
   (b) a heavy chain B and a light chain B, wherein the heavy chain B comprises a variable domain $V_HB$ and the light chain B comprises a variable domain $V_LB$, wherein $V_HB$ is linked to a dimerization domain $C_{H1}$ and $V_LB$ is linked to a dimerization domain $C_L$, wherein $C_{H1}$ and $C_L$ form a $C_{H1}/C_L$ dimer, wherein $C_{H1}$ has the amino acid sequence of a $C_{H1}$ domain comprised in SEQ ID NO: 9 and CL has the amino acid sequence of a CL domain comprised in SEQ ID NO: 8 and wherein $V_HB$ and $V_LB$ form a second paratope BB; and
   wherein $CH2_H$ is linked via a hinge region to a constant domain $C_H2A$, and $C_{H1}$ is linked via a hinge region to a constant domain $C_H2B$, and wherein $C_H2A$ is linked to a constant domain $C_H3A$ and $C_H2B$ is linked to a constant domain $C_H3B$; and wherein:
  (i) heavy chain A comprises one or more hole amino acid substitution(s) of knob-into-hole amino acid substitutions, wherein heavy chain A has reduced Protein A affinity as determined by Protein A chromatography and heavy chain B comprises one or more knob amino acid substitution(s) of knob-into-hole amino acid substitutions, or
  (ii) heavy chain B comprises one or more hole amino acid substitution(s) of knob-into-hole amino acid substitutions, wherein heavy chain B has reduced Protein A affinity as determined by Protein A chromatography and heavy chain A comprises one or more knob amino acid substitution(s) of knob-into-hole amino acid substitutions; and wherein heavy chain A dimerizes with heavy chain B; and wherein the antibody or antigen-binding fragment thereof is selectable by a method comprising a step of selecting for Protein A binding, and not comprising a step of selecting for the presence of a $C_{H1}$ domain or a $C_L$ domain.

2. The antibody or antigen-binding fragment thereof of claim 1, wherein the antibody or antigen-binding fragment thereof is multispecific.

3. The antibody or antigen-binding fragment thereof of claim 1, wherein paratopes AA and BB are not identical to each other.

4. The antibody or antigen-binding fragment thereof of claim 1, wherein:
  (a) heavy chain A comprises a further heavy chain variable domain $V_HX$ linked to $V_HA$ and light chain A comprises a further light chain variable domain $V_LX$ linked to $V_LA$, wherein $V_HX$ and $V_LX$ form a third paratope XX; and/or
  (b) heavy chain B comprises a further heavy chain variable domain $V_HY$ linked to $V_HB$ and light chain B comprises a further light chain variable domain $V_LY$ linked to $V_LB$, wherein $V_HY$ and $V_LY$ form a fourth paratope YY.

5. The antibody or antigen-binding fragment thereof of claim 1, wherein the antibody or antigen-binding fragment thereof comprises one or more of:
  (a) a T366Y mutation and optionally further an S354C and T166W mutation in one heavy chain, and a Y407T mutation and optionally further a Y349C, T366S, L368A, and Y407V mutation in the other heavy chain;
  (b) a T366W mutation in one heavy chain, and a T366S, L368A and Y407V mutation in the other heavy chain;
  (c) a F405L mutation in one heavy chain, and a K409R mutation in the other heavy chain;
  (d) a T350V, L351Y, F405A, and Y407V mutation in one heavy chain, and a T350V, T366L, K392L, and T394W mutation in the other heavy chain;
  (e) a K409D and K392D mutation in one heavy chain, and a D399K and E356K mutation in the other heavy chain;
  (f) a D221E, P228E, and L368E mutation in one heavy chain, and a D221R, P228R, and K409R mutation in the other heavy chain;
  (g) a S364H and F405A mutation in one heavy chain, and a Y349T and T394F mutation in the other heavy chain;
  (h) an Fc region or part thereof of one heavy chain from IgG3, and an Fc region or part thereof of the other heavy chain from IgG1, IgG2, or IgG4;
  (i) a H435R and Y436F mutation in one heavy chain, and a T407T mutation in the other heavy chain; and/or
  (j) a H435R mutation in one heavy chain, and no mutation in the other heavy chain.

6. The antibody or antigen-binding fragment thereof of claim 1, wherein
  (i) heavy chain A comprises one or more hole amino acid substitution(s) of knob-into-hole amino acid substitutions, and an IgG3 $C_H3$ domain or a H435R mutation, and heavy chain B comprises one or more knob amino acid substitution(s) of knob-into-hole amino acid substitutions and comprises an IgG1, 2 or 4 $C_H3$ domain if heavy chain A comprises the IgG3 $C_H3$ domain, or
  (ii) heavy chain B comprises one or more hole amino acid substitution(s) of knob-into-hole amino acid substitutions, and an IgG3 $C_H3$ domain or a H435R mutation, and heavy chain A comprises one or more knob amino acid substitution(s) of knob-into-hole amino acid substitutions and comprises an IgG1, 2 or 4 $C_H3$ domain if heavy chain B comprises the IgG3 $C_H3$ domain.

7. One or more polynucleotides encoding for an antibody or antigen-binding fragment thereof according to claim 2.

8. One or more expression vectors comprising the one or more polynucleotides of claim 7.

9. A cell comprising the one or more polynucleotides of claim 7.

10. A pharmaceutical composition comprising a pharmaceutically acceptable carrier and the antibody or antigen-binding fragment thereof according to claim 1.

11. A cell comprising the one or more expression vectors of claim 8.

12. A method of isolating the antibody or antigen-binding fragment thereof of claim 1,
  from a solution comprising the heavy chain A and the light chain A, and the heavy chain B and the light chain B according to claim 2
  by purifying the antibody or antigen-binding fragment thereof.

13. The method of claim 12, wherein the antibody or antigen-binding fragment thereof is purified by
  (a) selecting for Protein A binding.

14. The method of claim 12,
  the antibody or antigen-binding fragment thereof is purified by selecting for Protein A binding, characterized in that the method does not comprise selecting for the presence of a $C_{H1}$ domain or a $C_L$ domain, or for the absence of a $C_{H2}$ domain.

* * * * *

SEQUENCE LISTING

```
<160> NUMBER OF SEQ ID NOS: 33

<210> SEQ ID NO 1
<211> LENGTH: 112
<212> TYPE: PRT
<213> ORGANISM: Artificial Sequence
<220> FEATURE:
<223> OTHER INFORMATION: mutated MCH2

<400> SEQUENCE: 1

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
                20                  25                  30

Thr Gly Phe Ser Pro Arg Gln Ile Gln Val Ser Trp Leu Arg Glu Gly
            35                  40                  45

Lys Gln Val Gly Ser Gly Val Thr Thr Asp Gln Val Gln Ala Glu Ala
        50                  55                  60

Lys Glu Ser Gly Pro Thr Thr Tyr Lys Val Thr Ser Thr Leu Thr Ile
65                  70                  75                  80
```

```
Lys Glu Ser Asp Trp Leu Gly Gln Ser Met Phe Thr Cys Arg Val Asp
                85                  90                  95

His Arg Gly Leu Thr Phe Gln Gln Gln Ala Ser Ser Met Cys Val Pro
            100                 105                 110

<210> SEQ ID NO 2
<211> LENGTH: 107
<212> TYPE: PRT
<213> ORGANISM: Artificial Sequence
<220> FEATURE:
<223> OTHER INFORMATION: mutated ECH2

<400> SEQUENCE: 2

Val Ala Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala
            100                 105

<210> SEQ ID NO 3
<211> LENGTH: 220
<212> TYPE: PRT
<213> ORGANISM: Artificial Sequence
<220> FEATURE:
<223> OTHER INFORMATION: tetravalent spider antibody, light chains A

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                    165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 4
<211> LENGTH: 687
<212> TYPE: PRT
<213> ORGANISM: Artificial Sequence
<220> FEATURE:
<223> OTHER INFORMATION: tetravalent spider antibody, heavy chains

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Gly Gly Val Ile Ala Glu Leu Pro
        115                 120                 125

Pro Lys Val Ser Val Phe Val Pro Pro Arg Asp Gly Phe Phe Gly Asn
    130                 135                 140

Pro Arg Lys Ser Lys Leu Ile Cys Gln Ala Thr Gly Phe Ser Pro Arg
145                 150                 155                 160

Gln Ile Gln Val Ser Trp Leu Arg Glu Gly Lys Gln Val Gly Ser Gly
                165                 170                 175

Val Thr Thr Asp Gln Val Gln Ala Glu Ala Lys Glu Ser Gly Pro Thr
            180                 185                 190

Thr Tyr Lys Val Thr Ser Thr Leu Thr Ile Lys Glu Ser Asp Trp Leu
        195                 200                 205

Gly Gln Ser Met Phe Thr Cys Arg Val Asp His Arg Gly Leu Thr Phe
    210                 215                 220

Gln Gln Asn Ala Ser Ser Met Cys Val Pro Gly Gly Gly Ser Glu Val
225                 230                 235                 240

Gln Leu Val Gln Ser Gly Ala Glu Val Lys Lys Pro Gly Glu Ser Leu
                245                 250                 255

Lys Ile Ser Cys Lys Gly Ser Gly Tyr Ser Phe Thr Asp Tyr Tyr Met
            260                 265                 270

Lys Trp Ala Arg Gln Met Pro Gly Lys Gly Leu Glu Trp Met Gly Asp
        275                 280                 285

Ile Ile Pro Ser Ser Gly Ala Thr Phe Tyr Asn Gln Lys Phe Lys Gly
    290                 295                 300

Gln Val Thr Ile Ser Ala Asp Lys Ser Ile Ser Thr Thr Tyr Leu Gln
```

```
                305                 310                 315                 320
Trp Ser Ser Leu Lys Ala Ser Asp Thr Ala Met Tyr Tyr Cys Ala Arg
                325                 330                 335
Ser His Leu Leu Arg Ala Ser Trp Phe Ala Tyr Trp Gly Gln Gly Thr
                340                 345                 350
Met Val Thr Val Ser Ser Ala Ser Thr Lys Gly Pro Ser Val Phe Pro
                355                 360                 365
Leu Ala Pro Ser Ser Lys Ser Thr Ser Gly Gly Thr Ala Ala Leu Gly
            370                 375                 380
Cys Leu Val Lys Asp Tyr Phe Pro Glu Pro Val Thr Val Ser Trp Asn
385                 390                 395                 400
Ser Gly Ala Leu Thr Ser Gly Val His Thr Phe Pro Ala Val Leu Gln
                405                 410                 415
Ser Ser Gly Leu Tyr Ser Leu Ser Val Val Thr Val Pro Ser Ser
                420                 425                 430
Ser Leu Gly Thr Gln Thr Tyr Ile Cys Asn Val Asn His Lys Pro Ser
                435                 440                 445
Asn Thr Lys Val Asp Lys Lys Val Glu Pro Lys Ser Cys Asp Lys Thr
            450                 455                 460
His Thr Cys Pro Pro Cys Pro Ala Pro Glu Leu Leu Gly Gly Pro Ser
465                 470                 475                 480
Val Phe Leu Phe Pro Pro Lys Pro Lys Asp Thr Leu Met Ile Ser Arg
                485                 490                 495
Thr Pro Glu Val Thr Cys Val Val Val Asp Val Ser His Glu Asp Pro
                500                 505                 510
Glu Val Lys Phe Asn Trp Tyr Val Asp Gly Val Glu Val His Asn Ala
            515                 520                 525
Lys Thr Lys Pro Arg Glu Glu Gln Tyr Asn Ser Thr Tyr Arg Val Val
                530                 535                 540
Ser Val Leu Thr Val Leu His Gln Asp Trp Leu Asn Gly Lys Glu Tyr
545                 550                 555                 560
Lys Cys Lys Val Ser Asn Lys Ala Leu Pro Ala Pro Ile Glu Lys Thr
                565                 570                 575
Ile Ser Lys Ala Lys Gly Gln Pro Arg Glu Pro Gln Val Tyr Thr Leu
                580                 585                 590
Pro Pro Ser Arg Asp Glu Leu Thr Lys Asn Gln Val Ser Leu Thr Cys
            595                 600                 605
Leu Val Lys Gly Phe Tyr Pro Ser Asp Ile Ala Val Glu Trp Glu Ser
            610                 615                 620
Asn Gly Gln Pro Glu Asn Asn Tyr Lys Thr Thr Pro Pro Val Leu Asp
625                 630                 635                 640
Ser Asp Gly Ser Phe Phe Leu Tyr Ser Lys Leu Thr Val Asp Lys Ser
                645                 650                 655
Arg Trp Gln Gln Gly Asn Val Phe Ser Cys Ser Val Met His Glu Ala
                660                 665                 670
Leu His Asn His Tyr Thr Gln Lys Ser Leu Ser Leu Ser Pro Gly
                675                 680                 685

<210> SEQ ID NO 5
<211> LENGTH: 221
<212> TYPE: PRT
<213> ORGANISM: Artificial Sequence
<220> FEATURE:
<223> OTHER INFORMATION: tetravalent spider antibody, light chains B
```

```
<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ile Ala
            100                 105                 110

Glu Leu Pro Pro Lys Val Ser Val Phe Val Pro Pro Arg Asp Gly Phe
        115                 120                 125

Phe Gly Asn Pro Arg Lys Ser Lys Leu Ile Cys Gln Ala Thr Gly Phe
    130                 135                 140

Ser Pro Arg Gln Ile Gln Val Ser Trp Leu Arg Glu Gly Lys Gln Val
145                 150                 155                 160

Gly Ser Gly Val Thr Thr Asp Gln Val Gln Ala Glu Ala Lys Glu Ser
                165                 170                 175

Gly Pro Thr Thr Tyr Lys Val Thr Ser Thr Leu Thr Ile Lys Glu Ser
            180                 185                 190

Asp Trp Leu Gly Gln Ser Met Phe Thr Cys Arg Val Asp His Arg Gly
        195                 200                 205

Leu Thr Phe Gln Gln Asn Ala Ser Ser Met Cys Val Pro
    210                 215                 220

<210> SEQ ID NO 6
<211> LENGTH: 226
<212> TYPE: PRT
<213> ORGANISM: Artificial Sequence
<220> FEATURE:
<223> OTHER INFORMATION: bispecific IgG1 antibody, light chain A

<400> SEQUENCE: 6

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Thr Val Ile Ala Glu Leu Pro Pro Lys Val Ser Val Phe Val Pro
        115                 120                 125

Pro Arg Asp Gly Phe Phe Gly Asn Pro Arg Lys Ser Lys Leu Ile Cys
```

```
            130                 135                 140
Gln Ala Thr Gly Phe Ser Pro Arg Gln Ile Gln Val Ser Trp Leu Arg
145                 150                 155                 160

Glu Gly Lys Gln Val Gly Ser Gly Val Thr Thr Asp Gln Val Gln Ala
                165                 170                 175

Glu Ala Lys Glu Ser Gly Pro Thr Thr Tyr Lys Val Thr Ser Thr Leu
            180                 185                 190

Thr Ile Lys Glu Ser Asp Trp Leu Gly Gln Ser Met Phe Thr Cys Arg
        195                 200                 205

Val Asp His Arg Gly Leu Thr Phe Gln Gln Gln Ala Ser Ser Met Cys
        210                 215                 220

Val Pro
225

<210> SEQ ID NO 7
<211> LENGTH: 462
<212> TYPE: PRT
<213> ORGANISM: Artificial Sequence
<220> FEATURE:
<223> OTHER INFORMATION: bispecific IgG1 antibody, heavy chain A

<400> SEQUENCE: 7

Gln Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Ser
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Arg Ser Leu Thr Ser Glu Asp Ser Ala Val Tyr Phe Cys
                85                  90                  95

Ala Met Arg Arg Ser Tyr Trp Gly Gln Gly Thr Leu Val Thr Val Ser
            100                 105                 110

Ala Ala Ser Thr Lys Gly Pro Val Ile Ala Glu Leu Pro Pro Lys Val
        115                 120                 125

Ser Val Phe Val Pro Pro Arg Asp Gly Phe Phe Gly Asn Pro Arg Lys
    130                 135                 140

Ser Lys Leu Ile Cys Gln Ala Thr Gly Phe Ser Pro Arg Gln Ile Gln
145                 150                 155                 160

Val Ser Trp Leu Arg Glu Gly Lys Gln Val Gly Ser Gly Val Thr Thr
                165                 170                 175

Asp Gln Val Gln Ala Glu Ala Lys Glu Ser Gly Pro Thr Thr Tyr Lys
            180                 185                 190

Val Thr Ser Thr Leu Thr Ile Lys Glu Ser Asp Trp Leu Gly Gln Ser
        195                 200                 205

Met Phe Thr Cys Arg Val Asp His Arg Gly Leu Thr Phe Gln Gln Gln
    210                 215                 220

Ala Ser Ser Met Cys Val Pro Glu Pro Lys Ser Ala Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
```

```
                260               265                270
    Pro Glu Val Thr Cys Val Val Val Asp Val Ser His Glu Asp Pro Glu
                275               280                285

Val Lys Phe Asn Trp Tyr Val Asp Gly Val Glu Val His Asn Ala Lys
                290               295                300

Thr Lys Pro Arg Glu Glu Gln Tyr Asn Ser Thr Tyr Arg Val Val Ser
    305               310               315                320

Val Leu Thr Val Leu His Gln Asp Trp Leu Asn Gly Lys Glu Tyr Lys
                    325               330                335

Cys Lys Val Ser Asn Lys Ala Leu Pro Ala Pro Ile Glu Lys Thr Ile
                    340               345               350

Ser Lys Ala Lys Gly Gln Pro Arg Glu Pro Gln Val Cys Thr Leu Pro
                355               360               365

Pro Ser Arg Asp Glu Leu Thr Lys Asn Gln Val Ser Leu Ser Cys Ala
        370               375               380

Val Lys Gly Phe Tyr Pro Ser Asp Ile Ala Val Glu Trp Glu Ser Asn
    385               390               395                400

Gly Gln Pro Glu Asn Asn Tyr Lys Thr Thr Pro Pro Val Leu Asp Ser
                    405               410                415

Asp Gly Ser Phe Phe Leu Val Ser Lys Leu Thr Val Asp Lys Ser Arg
                    420               425                430

Trp Gln Gln Gly Asn Val Phe Ser Cys Ser Val Met His Glu Ala Leu
                    435               440               445

His Asn His Tyr Thr Gln Lys Ser Leu Ser Leu Ser Pro Gly
        450               455               460

<210> SEQ ID NO 8
<211> LENGTH: 214
<212> TYPE: PRT
<213> ORGANISM: Artificial Sequence
<220> FEATURE:
<223> OTHER INFORMATION: bispecific IgG1 antibody, light chain B

<400> SEQUENCE: 8

Asp Ile Val Leu Thr Gln Ser Pro Ala Thr Leu Ser Val Thr Pro Gly
    1               5                   10                  15

Asp Ser Val Ser Leu Ser Cys Arg Ala Ser Gln Ser Ile Ser Asn Tyr
                    20                  25                  30

Leu His Trp Tyr Gln Gln Lys Ser His Glu Ser Pro Arg Leu Leu Ile
                35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
    65                  70                  75                  80

Glu Asp Phe Gly Met Tyr Phe Cys Gln Gln Ser Lys Ser Trp Pro Arg
                    85                  90                  95

Thr Phe Gly Gly Gly Thr Glu Leu Glu Ile Lys Arg Thr Val Ala Ala
                    100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
    145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 447
<212> TYPE: PRT
<213> ORGANISM: Artificial Sequence
<220> FEATURE:
<223> OTHER INFORMATION: bispecific IgG1 antibody, heavy chain B

<400> SEQUENCE: 9

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Asp Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Phe Asp Tyr Gly Ser Ser Leu Asp Cys Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr

```
            305                 310                 315                 320
Lys Cys Lys Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Cys Arg Asp Glu Leu Thr Lys Asn Gln Val Ser Leu Trp Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn Arg Phe Thr Gln Lys Ser Leu Ser Leu Ser Pro Gly
            435                 440                 445
```

<210> SEQ ID NO 10
<211> LENGTH: 225
<212> TYPE: PRT
<213> ORGANISM: Artificial Sequence
<220> FEATURE:
<223> OTHER INFORMATION: bispecific IgG1 antibody, light chain A

<400> SEQUENCE: 10

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
            20                  25                  30
Gly Gln Ser Tyr Met His Trp Tyr Gln Gln Lys Ala Gly Gln Pro Pro
            35                  40                  45
Lys Leu Leu Ile Tyr Leu Ala Ser Asn Leu Glu Ser Gly Val Pro Ala
            50                  55                  60
Arg Phe Ser Gly Ser Gly Ser Arg Thr Asp Phe Thr Leu Thr Ile Asp
65                  70                  75                  80
Pro Val Gln Ala Glu Asp Ala Ala Thr Tyr Tyr Cys Gln Gln Asn Ala
            85                  90                  95
Glu Asp Ser Arg Thr Phe Gly Gly Gly Thr Lys Leu Glu Ile Lys Arg
            100                 105                 110
Thr Val Ile Ala Glu Leu Pro Pro Lys Val Ser Val Phe Val Pro Pro
            115                 120                 125
Arg Asp Gly Phe Phe Gly Asn Pro Arg Lys Ser Lys Leu Ile Cys Gln
            130                 135                 140
Ala Thr Gly Phe Ser Pro Arg Gln Ile Gln Val Ser Trp Leu Arg Glu
145                 150                 155                 160
Gly Lys Gln Val Gly Ser Gly Val Thr Thr Asp Gln Val Gln Ala Glu
            165                 170                 175
Ala Lys Glu Ser Gly Pro Thr Thr Tyr Lys Val Thr Ser Thr Leu Thr
            180                 185                 190
Ile Lys Glu Ser Asp Trp Leu Gly Gln Ser Met Phe Thr Cys Arg Val
            195                 200                 205
Asp His Arg Gly Leu Thr Phe Gln Gln Gln Ala Ser Ser Met Cys Val
            210                 215                 220
Pro
```

<210> SEQ ID NO 11
<211> LENGTH: 467
<212> TYPE: PRT
<213> ORGANISM: Artificial Sequence
<220> FEATURE:
<223> OTHER INFORMATION: bispecific IgG1 antibody, heavy chain A

<400> SEQUENCE: 11

```
Glu Val Gln Leu Lys Glu Ser Gly Pro Gly Leu Val Ala Pro Gly Gly
1               5                   10                  15
Ser Leu Ser Ile Thr Cys Thr Val Ser Gly Phe Ser Leu Thr Asp Ser
            20                  25                  30
Ser Ile Asn Trp Val Arg Gln Pro Pro Gly Lys Gly Leu Glu Trp Leu
        35                  40                  45
Gly Met Ile Trp Gly Asp Gly Arg Ile Asp Tyr Ala Asp Ala Leu Lys
    50                  55                  60
Ser Arg Leu Ser Ile Ser Lys Asp Ser Ser Lys Ser Gln Val Phe Leu
65                  70                  75                  80
Glu Met Thr Ser Leu Arg Thr Asp Asp Thr Ala Thr Tyr Tyr Cys Ala
                85                  90                  95
Arg Asp Gly Tyr Phe Pro Tyr Ala Met Asp Phe Trp Gly Gln Gly Thr
            100                 105                 110
Ser Val Thr Val Ser Ser Ala Ser Thr Lys Gly Pro Val Ile Ala Glu
        115                 120                 125
Leu Pro Pro Lys Val Ser Val Phe Val Pro Pro Arg Asp Gly Phe Phe
130                 135                 140
Gly Asn Pro Arg Lys Ser Lys Leu Ile Cys Gln Ala Thr Gly Phe Ser
145                 150                 155                 160
Pro Arg Gln Ile Gln Val Ser Trp Leu Arg Glu Gly Lys Gln Val Gly
                165                 170                 175
Ser Gly Val Thr Thr Asp Gln Val Gln Ala Glu Ala Lys Glu Ser Gly
            180                 185                 190
Pro Thr Thr Tyr Lys Val Thr Ser Thr Leu Thr Ile Lys Glu Ser Asp
        195                 200                 205
Trp Leu Gly Gln Ser Met Phe Thr Cys Arg Val Asp His Arg Gly Leu
    210                 215                 220
Thr Phe Gln Gln Gln Ala Ser Ser Met Cys Val Pro Glu Pro Lys Ser
225                 230                 235                 240
Ala Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
```

```
                355                 360                 365
Val Cys Thr Leu Pro Pro Ser Arg Asp Glu Leu Thr Lys Asn Gln Val
370                 375                 380

Ser Leu Ser Cys Ala Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Val Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly
465

<210> SEQ ID NO 12
<211> LENGTH: 214
<212> TYPE: PRT
<213> ORGANISM: Artificial Sequence
<220> FEATURE:
<223> OTHER INFORMATION: bispecific IgG1 antibody, light chain B

<400> SEQUENCE: 12

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
                20                  25                  30

Leu Ser Trp Phe Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 13
<211> LENGTH: 452
<212> TYPE: PRT
```

<213> ORGANISM: Artificial Sequence
<220> FEATURE:
<223> OTHER INFORMATION: bispecific IgG1 antibody, heavy chain B

<400> SEQUENCE: 13

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                      385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn Arg Phe Thr Gln Lys Ser Leu Ser
                435                 440                 445

Leu Ser Pro Gly
            450

<210> SEQ ID NO 14
<211> LENGTH: 226
<212> TYPE: PRT
<213> ORGANISM: Artificial Sequence
<220> FEATURE:
<223> OTHER INFORMATION: bivalent Fab, light chain A

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
                20                  25                  30

Asn Ala Asn Thr Tyr Leu Ser Trp Tyr Leu Gln Lys Pro Gly Gln Ser
                35                  40                  45

Pro Gln Ser Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
                100                 105                 110

Arg Thr Val Ile Ala Glu Leu Pro Pro Lys Val Ser Val Phe Val Pro
                115                 120                 125

Pro Arg Asp Gly Phe Phe Gly Asn Pro Arg Lys Ser Lys Leu Ile Cys
            130                 135                 140

Gln Ala Thr Gly Phe Ser Pro Arg Gln Ile Gln Val Ser Trp Leu Arg
145                 150                 155                 160

Glu Gly Lys Gln Val Gly Ser Gly Val Thr Thr Asp Gln Val Gln Ala
                165                 170                 175

Glu Ala Lys Glu Ser Gly Pro Thr Thr Tyr Lys Val Thr Ser Thr Leu
                180                 185                 190

Thr Ile Lys Glu Ser Asp Trp Leu Gly Gln Ser Met Phe Thr Cys Arg
                195                 200                 205

Val Asp His Arg Gly Leu Thr Phe Gln Gln Asn Ala Ser Ser Met Cys
                210                 215                 220

Val Pro
225

<210> SEQ ID NO 15
<211> LENGTH: 473
<212> TYPE: PRT
<213> ORGANISM: Artificial Sequence
<220> FEATURE:
<223> OTHER INFORMATION: bivalent Fab, heavy chain

<400> SEQUENCE: 15
```

```
Gln Val Gln Leu Val Glu Ser Gly Gly Val Val Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
            35                  40                  45

Ala Gln Ile Lys Asp Lys Ser Asn Ser Tyr Ala Thr Tyr Tyr Ala Asp
        50                  55                  60

Ser Val Lys Gly Arg Phe Thr Ile Ser Arg Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser Gly Gly Val Ile Ala Glu Leu
            115                 120                 125

Pro Pro Lys Val Ser Val Phe Val Pro Pro Arg Asp Gly Phe Phe Gly
        130                 135                 140

Asn Pro Arg Lys Ser Lys Leu Ile Cys Gln Ala Thr Gly Phe Ser Pro
145                 150                 155                 160

Arg Gln Ile Gln Val Ser Trp Leu Arg Glu Gly Lys Gln Val Gly Ser
            165                 170                 175

Gly Val Thr Thr Asp Gln Val Gln Ala Glu Ala Lys Glu Ser Gly Pro
            180                 185                 190

Thr Thr Tyr Lys Val Thr Ser Thr Leu Thr Ile Lys Glu Ser Asp Trp
        195                 200                 205

Leu Gly Gln Ser Met Phe Thr Cys Arg Val Asp His Arg Gly Leu Thr
210                 215                 220

Phe Gln Gln Asn Ala Ser Ser Met Cys Val Pro Gly Gly Gly Ser Glu
225                 230                 235                 240

Val Gln Leu Val Gln Ser Gly Ala Glu Val Lys Lys Pro Gly Glu Ser
            245                 250                 255

Leu Lys Ile Ser Cys Lys Gly Ser Gly Tyr Ser Phe Thr Asp Tyr Tyr
        260                 265                 270

Met Lys Trp Ala Arg Gln Met Pro Gly Lys Gly Leu Glu Trp Met Gly
        275                 280                 285

Asp Ile Ile Pro Ser Ser Gly Ala Thr Phe Tyr Asn Gln Lys Phe Lys
        290                 295                 300

Gly Gln Val Thr Ile Ser Ala Asp Lys Ser Ile Ser Thr Thr Tyr Leu
305                 310                 315                 320

Gln Trp Ser Ser Leu Lys Ala Ser Asp Thr Ala Met Tyr Tyr Cys Ala
            325                 330                 335

Arg Ser His Leu Leu Arg Ala Ser Trp Phe Ala Tyr Trp Gly Gln Gly
            340                 345                 350

Thr Met Val Thr Val Ser Ala Ser Thr Lys Gly Pro Ser Val Phe
            355                 360                 365

Pro Leu Ala Pro Ser Ser Lys Ser Thr Ser Gly Gly Thr Ala Ala Leu
370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
```

```
                    420                 425                 430
Ser Ser Leu Gly Thr Gln Thr Tyr Ile Cys Asn Val Asn His Lys Pro
            435                 440                 445
Ser Asn Thr Lys Val Asp Lys Lys Val Glu Pro Lys Ser Cys Asp Lys
        450                 455                 460
Thr His Thr His His His His His His
465                 470

<210> SEQ ID NO 16
<211> LENGTH: 220
<212> TYPE: PRT
<213> ORGANISM: Artificial Sequence
<220> FEATURE:
<223> OTHER INFORMATION: bivalent Fab, light chain B

<400> SEQUENCE: 16

Asp Ile Val Met Thr Gln Ser Pro Asp Ser Leu Ala Val Ser Leu Gly
1               5                   10                  15
Glu Arg Ala Thr Ile Asn Cys Glu Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Pro Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Ser Tyr Pro Tyr Thr Phe Gly Gln Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 17
<211> LENGTH: 226
<212> TYPE: PRT
<213> ORGANISM: Artificial Sequence
<220> FEATURE:
<223> OTHER INFORMATION: bivalent bispecific antibody, light chain LC1

<400> SEQUENCE: 17

Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Val His Asn
            20                  25                  30
```

-continued

Asn Ala Asn Thr Tyr Leu Ser Trp Tyr Leu Gln Lys Pro Gly Gln Ser
             35                  40                  45

Pro Gln Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Ser Gly Thr Lys Val Glu Ile Lys
                100                 105                 110

Arg Thr Val Ile Ala Glu Leu Pro Pro Lys Val Ser Val Phe Val Pro
            115                 120                 125

Pro Arg Asp Gly Phe Phe Gly Asn Pro Arg Lys Ser Lys Leu Ile Cys
130                 135                 140

Gln Ala Thr Gly Phe Ser Pro Arg Gln Ile Gln Val Ser Trp Leu Arg
145                 150                 155                 160

Glu Gly Lys Gln Val Gly Ser Gly Val Thr Thr Asp Gln Val Gln Ala
                165                 170                 175

Glu Ala Lys Glu Ser Gly Pro Thr Thr Tyr Lys Val Thr Ser Thr Leu
            180                 185                 190

Thr Ile Lys Glu Ser Asp Trp Leu Gly Gln Ser Met Phe Thr Cys Arg
        195                 200                 205

Val Asp His Arg Gly Leu Thr Phe Gln Gln Asn Ala Ser Ser Met Cys
    210                 215                 220

Val Pro
225

<210> SEQ ID NO 18
<211> LENGTH: 685
<212> TYPE: PRT
<213> ORGANISM: Artificial Sequence
<220> FEATURE:
<223> OTHER INFORMATION: bivalent bispecific antibody, heavy chain HC1

<400> SEQUENCE: 18

Gln Val Gln Leu Val Glu Ser Gly Gly Gly Val Gln Pro Gly Arg
 1               5                  10                  15

Ser Leu Arg Leu Ser Cys Ala Ala Ser Gly Phe Thr Phe Thr Lys Ala
             20                  25                  30

Trp Met His Trp Val Arg Gln Ala Pro Gly Lys Gln Leu Glu Trp Val
         35                  40                  45

Ala Gln Ile Lys Asp Lys Ser Asn Ser Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Arg Gly Val Tyr Tyr Ala Leu Ser Pro Phe Asp Tyr Trp Gly
                100                 105                 110

Gln Gly Thr Leu Val Thr Val Ser Ser Gly Gly Val Ile Ala Glu Leu
            115                 120                 125

Pro Pro Lys Val Ser Val Phe Val Pro Pro Arg Asp Gly Phe Phe Gly
130                 135                 140

Asn Pro Arg Lys Ser Lys Leu Ile Cys Gln Ala Thr Gly Phe Ser Pro
145                 150                 155                 160

```
Arg Gln Ile Gln Val Ser Trp Leu Arg Glu Gly Lys Val Gly Ser
            165                 170                 175

Gly Val Thr Thr Asp Gln Val Gln Ala Glu Ala Lys Glu Ser Gly Pro
        180                 185                 190

Thr Thr Tyr Lys Val Thr Ser Thr Leu Thr Ile Lys Glu Ser Asp Trp
        195                 200                 205

Leu Gly Gln Ser Met Phe Thr Cys Arg Val Asp His Arg Gly Leu Thr
210                 215                 220

Phe Gln Gln Asn Ala Ser Ser Met Cys Val Pro Gly Gly Ser Glu
225                 230                 235                 240

Val Gln Leu Val Gln Ser Gly Ala Glu Val Lys Lys Pro Gly Glu Ser
                245                 250                 255

Leu Lys Ile Ser Cys Lys Gly Ser Gly Tyr Ser Phe Thr Asp Tyr Tyr
                260                 265                 270

Met Lys Trp Ala Arg Gln Met Pro Gly Lys Gly Leu Glu Trp Met Gly
                275                 280                 285

Asp Ile Ile Pro Ser Ser Gly Ala Thr Phe Tyr Asn Gln Lys Phe Lys
                290                 295                 300

Gly Gln Val Thr Ile Ser Ala Asp Lys Ser Ile Ser Thr Thr Tyr Leu
305                 310                 315                 320

Gln Trp Ser Ser Leu Lys Ala Ser Asp Thr Ala Met Tyr Tyr Cys Ala
                325                 330                 335

Arg Ser His Leu Leu Arg Ala Ser Trp Phe Ala Tyr Trp Gly Gln Gly
                340                 345                 350

Thr Met Val Thr Val Ser Ser Ala Ser Thr Lys Gly Pro Ser Val Phe
                355                 360                 365

Pro Leu Ala Pro Cys Ser Arg Ser Thr Ser Glu Ser Thr Ala Ala Leu
                370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
                420                 425                 430

Ser Ser Leu Gly Thr Lys Thr Tyr Thr Cys Asn Val Asp His Lys Pro
                435                 440                 445

Ser Asn Thr Lys Val Asp Lys Arg Val Glu Ser Lys Tyr Gly Pro Pro
                450                 455                 460

Cys Pro Pro Cys Pro Ala Pro Glu Phe Glu Gly Gly Pro Ser Val Phe
465                 470                 475                 480

Leu Phe Pro Pro Lys Pro Lys Asp Thr Leu Met Ile Ser Arg Thr Pro
                485                 490                 495

Glu Val Thr Cys Val Val Val Asp Val Ser Gln Glu Asp Pro Glu Val
                500                 505                 510

Gln Phe Asn Trp Tyr Val Asp Gly Val Glu Val His Asn Ala Lys Thr
                515                 520                 525

Lys Pro Arg Glu Glu Gln Phe Asn Ser Thr Tyr Arg Val Val Ser Val
                530                 535                 540

Leu Thr Val Leu His Gln Asp Trp Leu Asn Gly Lys Glu Tyr Lys Cys
545                 550                 555                 560

Lys Val Ser Asn Lys Gly Leu Pro Ser Ser Ile Glu Lys Thr Ile Ser
                565                 570                 575

Lys Ala Lys Gly Gln Pro Arg Glu Pro Gln Val Tyr Thr Leu Pro Pro
```

```
                580             585             590
Ser Gln Glu Glu Met Thr Lys Asn Gln Val Ser Leu Thr Cys Leu Val
            595                 600                 605

Lys Gly Phe Tyr Pro Ser Asp Ile Ala Val Glu Trp Glu Ser Asn Gly
            610                 615                 620

Gln Pro Glu Asn Asn Tyr Lys Thr Thr Pro Val Leu Asp Ser Asp
625                 630                 635                 640

Gly Ser Phe Phe Leu Tyr Ser Arg Leu Thr Val Asp Lys Ser Arg Trp
            645                 650                 655

Gln Glu Gly Asn Val Phe Ser Cys Ser Val Met His Glu Ala Leu His
            660                 665                 670

Asn His Tyr Thr Gln Lys Ser Leu Ser Leu Ser Leu Gly
            675                 680                 685

<210> SEQ ID NO 19
<211> LENGTH: 448
<212> TYPE: PRT
<213> ORGANISM: Artificial Sequence
<220> FEATURE:
<223> OTHER INFORMATION: bivalent bispecific antibody, light chain LC2

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
```

```
               260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn Arg Phe Thr Gln Lys Ser Leu Ser Leu Ser Leu Gly
        435                 440                 445

<210> SEQ ID NO 20
<211> LENGTH: 367
<212> TYPE: PRT
<213> ORGANISM: Artificial Sequence
<220> FEATURE:
<223> OTHER INFORMATION: CH2E-pseudo-CODV antibody, chain 1

<400> SEQUENCE: 20

Glu Val Gln Leu Lys Glu Ser Gly Pro Gly Leu Val Ala Pro Gly Gly
1               5                   10                  15
Ser Leu Ser Ile Thr Cys Thr Val Ser Gly Phe Ser Leu Thr Asp Ser
            20                  25                  30
Ser Ile Asn Trp Val Arg Gln Pro Pro Gly Lys Gly Leu Glu Trp Leu
        35                  40                  45
Gly Met Ile Trp Gly Asp Gly Arg Ile Asp Tyr Ala Asp Ala Leu Lys
    50                  55                  60
Ser Arg Leu Ser Ile Ser Lys Asp Ser Ser Lys Ser Gln Val Phe Leu
65                  70                  75                  80
Glu Met Thr Ser Leu Arg Thr Asp Asp Thr Ala Thr Tyr Tyr Cys Ala
                85                  90                  95
Arg Asp Gly Tyr Phe Pro Tyr Ala Met Asp Phe Trp Gly Gln Gly Thr
            100                 105                 110
Ser Val Thr Val Ser Ser Gln Val Gln Leu Gln Gln Ser Gly Pro
        115                 120                 125
Glu Leu Val Lys Pro Gly Ala Ser Val Lys Ile Ser Cys Lys Ala Ser
    130                 135                 140
Gly Tyr Ser Phe Thr Ser Tyr Trp Ile His Trp Ile Lys Gln Arg Pro
145                 150                 155                 160
Gly Gln Gly Leu Glu Trp Ile Gly Met Ile Asp Pro Ser Asp Gly Glu
                165                 170                 175
Thr Arg Leu Asn Gln Arg Phe Gln Gly Arg Ala Thr Leu Thr Val Asp
```

```
                180                 185                 190
Glu Ser Thr Ser Thr Ala Tyr Met Gln Leu Arg Ser Pro Thr Ser Glu
            195                 200                 205

Asp Ser Ala Val Tyr Tyr Cys Thr Arg Leu Lys Glu Tyr Gly Asn Tyr
        210                 215                 220

Asp Ser Phe Tyr Phe Asp Val Trp Gly Ala Gly Thr Leu Val Thr Val
225                 230                 235                 240

Ser Ser Arg Thr Ala Ser Thr Lys Gly Pro Val Ala Ser Arg Asp Phe
            245                 250                 255

Thr Pro Pro Thr Val Lys Ile Leu Gln Ser Ser Cys Asp Gly Gly Gly
        260                 265                 270

His Phe Pro Pro Thr Ile Gln Leu Leu Cys Leu Val Ser Gly Tyr Thr
        275                 280                 285

Pro Gly Thr Ile Gln Ile Thr Trp Leu Glu Asp Gly Gln Val Met Asp
        290                 295                 300

Val Asp Leu Ser Thr Ala Ser Thr Thr Gln Glu Gly Glu Leu Ala Ser
305                 310                 315                 320

Thr Gln Ser Glu Leu Thr Leu Ser Gln Lys His Trp Leu Ser Asp Arg
            325                 330                 335

Thr Tyr Thr Cys Gln Val Thr Tyr Gln Gly His Thr Phe Glu Asp Ser
            340                 345                 350

Thr Lys Lys Cys Ala Gly Ser His His His His His His
            355                 360                 365

<210> SEQ ID NO 21
<211> LENGTH: 339
<212> TYPE: PRT
<213> ORGANISM: Artificial Sequence
<220> FEATURE:
<223> OTHER INFORMATION: CH2E-pseudo-CODV antibody, chain 2

<400> SEQUENCE: 21

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
            85                  90                  95

Thr Phe Gly Gly Gly Thr Lys Leu Glu Ile Lys Gly Gln Pro Lys Ala
        100                 105                 110

Ala Pro Asp Ile Val Leu Thr Gln Ser Pro Ala Ser Leu Ala Val Ser
        115                 120                 125

Leu Gly Gln Arg Ala Thr Ile Ser Cys Arg Ala Ser Glu Ser Val Asp
    130                 135                 140

Ser Tyr Gly Gln Ser Tyr Met His Trp Tyr Gln Gln Lys Ala Gly Gln
145                 150                 155                 160

Pro Pro Lys Leu Leu Ile Tyr Leu Ala Ser Asn Leu Glu Ser Gly Val
            165                 170                 175

Pro Ala Arg Phe Ser Gly Ser Gly Ser Arg Thr Asp Phe Thr Leu Thr
```

```
            180                 185                 190
Ile Asp Pro Val Gln Ala Glu Asp Ala Ala Thr Tyr Tyr Cys Gln Gln
            195                 200                 205

Asn Ala Glu Asp Ser Arg Thr Phe Gly Gly Gly Thr Lys Leu Glu Ile
        210                 215                 220

Lys Thr Lys Gly Pro Ser Arg Thr Val Ala Ser Arg Asp Phe Thr Pro
225                 230                 235                 240

Pro Thr Val Lys Ile Leu Gln Ser Ser Cys Asp Gly Gly His Phe
                245                 250                 255

Pro Pro Thr Ile Gln Leu Leu Cys Leu Val Ser Gly Tyr Thr Pro Gly
                260                 265                 270

Thr Ile Gln Ile Thr Trp Leu Glu Asp Gly Gln Val Met Asp Val Asp
            275                 280                 285

Leu Ser Thr Ala Ser Thr Thr Gln Glu Gly Glu Leu Ala Ser Thr Gln
        290                 295                 300

Ser Glu Leu Thr Leu Ser Gln Lys His Trp Leu Ser Asp Arg Thr Tyr
305                 310                 315                 320

Thr Cys Gln Val Thr Tyr Gln Gly His Thr Phe Glu Asp Ser Thr Lys
                325                 330                 335

Lys Cys Ala

<210> SEQ ID NO 22
<211> LENGTH: 338
<212> TYPE: PRT
<213> ORGANISM: Artificial Sequence
<220> FEATURE:
<223> OTHER INFORMATION: pseudo hinge-CH2E-hybrid-Fab2, heavy chain A

<400> SEQUENCE: 22

Val Gln Leu Gln Gln Ser Gly Pro Glu Leu Val Lys Pro Gly Ala Ser
1               5                   10                  15

Val Lys Ile Ser Cys Lys Ala Ser Gly Tyr Ser Phe Thr Ser Tyr Trp
            20                  25                  30

Ile His Trp Ile Lys Gln Arg Pro Gly Gln Gly Leu Glu Trp Ile Gly
        35                  40                  45

Met Ile Asp Pro Ser Asp Gly Glu Thr Arg Leu Asn Gln Arg Phe Gln
    50                  55                  60

Gly Arg Ala Thr Leu Thr Val Asp Glu Ser Thr Ser Thr Ala Tyr Met
65                  70                  75                  80

Gln Leu Arg Ser Pro Thr Ser Glu Asp Ser Ala Val Tyr Tyr Cys Thr
                85                  90                  95

Arg Leu Lys Glu Tyr Gly Asn Tyr Asp Ser Phe Tyr Phe Asp Val Trp
            100                 105                 110

Gly Ala Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Val Glu Pro Lys Ser
    210                 215                 220

Cys Gly Ser Gly Ser Gly Ser Val Ala Ser Arg Asp Phe Thr Pro Pro
225                 230                 235                 240

Thr Val Lys Ile Leu Gln Ser Ser Cys Asp Gly Gly His Phe Pro
                245                 250                 255

Pro Thr Ile Gln Leu Leu Cys Leu Val Ser Gly Tyr Thr Pro Gly Thr
                260                 265                 270

Ile Gln Ile Thr Trp Leu Glu Asp Gly Gln Val Met Asp Val Asp Leu
                275                 280                 285

Ser Thr Ala Ser Thr Thr Gln Glu Gly Glu Leu Ala Ser Thr Gln Ser
    290                 295                 300

Glu Leu Thr Leu Ser Gln Lys His Trp Leu Ser Asp Arg Thr Tyr Thr
305                 310                 315                 320

Cys Gln Val Thr Tyr Gln Gly His Thr Phe Glu Asp Ser Thr Lys Lys
                325                 330                 335

Cys Ala

<210> SEQ ID NO 23
<211> LENGTH: 214
<212> TYPE: PRT
<213> ORGANISM: Artificial Sequence
<220> FEATURE:
<223> OTHER INFORMATION: pseudo hinge-CH2E-hybrid-Fab2, light chain A

<400> SEQUENCE: 23

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 359
<212> TYPE: PRT
<213> ORGANISM: Artificial Sequence
<220> FEATURE:
<223> OTHER INFORMATION: pseudo hinge-CH2E-hybrid-Fab2, heavy chain B

<400> SEQUENCE: 24

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Gly Ser Gly Ser Gly Ser Val Ile Ala Glu
        115                 120                 125

Leu Pro Pro Lys Val Ser Val Phe Val Pro Pro Arg Asp Gly Phe Phe
130                 135                 140

Gly Asn Pro Arg Lys Ser Lys Leu Ile Cys Gln Ala Thr Gly Phe Ser
145                 150                 155                 160

Pro Arg Gln Ile Gln Val Ser Trp Leu Arg Glu Gly Lys Gln Val Gly
                165                 170                 175

Ser Gly Val Thr Thr Asp Gln Val Gln Ala Glu Ala Lys Glu Ser Gly
            180                 185                 190

Pro Thr Thr Tyr Lys Val Thr Ser Thr Leu Thr Ile Lys Glu Ser Asp
        195                 200                 205

Trp Leu Gly Gln Ser Met Phe Thr Cys Arg Val Asp His Arg Gly Leu
    210                 215                 220

Thr Phe Gln Gln Gln Ala Ser Ser Met Cys Val Pro Gly Ser Gly Ser
225                 230                 235                 240

Gly Ser Val Ala Ser Arg Asp Phe Thr Pro Pro Thr Val Lys Ile Leu
                245                 250                 255

Gln Ser Ser Cys Asp Gly Gly Gly His Phe Pro Pro Thr Ile Gln Leu
            260                 265                 270

Leu Cys Leu Val Ser Gly Tyr Thr Pro Gly Thr Ile Gln Ile Thr Trp
        275                 280                 285

Leu Glu Asp Gly Gln Val Met Asp Val Asp Leu Ser Thr Ala Ser Thr
    290                 295                 300

Thr Gln Glu Gly Glu Leu Ala Ser Thr Gln Ser Glu Leu Thr Leu Ser
305                 310                 315                 320

Gln Lys His Trp Leu Ser Asp Arg Thr Tyr Thr Cys Gln Val Thr Tyr
                325                 330                 335

Gln Gly His Thr Phe Glu Asp Ser Thr Lys Lys Cys Ala Gly Ser His
            340                 345                 350

His His His His His His
        355
```

<210> SEQ ID NO 25
<211> LENGTH: 225
<212> TYPE: PRT
<213> ORGANISM: Artificial Sequence
<220> FEATURE:
<223> OTHER INFORMATION: pseudo hinge-CH2E-hybrid-Fab2, light chain B

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Arg
            100                 105                 110

Thr Val Ile Ala Glu Leu Pro Pro Lys Val Ser Val Phe Val Pro Pro
        115                 120                 125

Arg Asp Gly Phe Phe Gly Asn Pro Arg Lys Ser Lys Leu Ile Cys Gln
    130                 135                 140

Ala Thr Gly Phe Ser Pro Arg Gln Ile Gln Val Ser Trp Leu Arg Glu
145                 150                 155                 160

Gly Lys Gln Val Gly Ser Gly Val Thr Thr Asp Gln Val Gln Ala Glu
                165                 170                 175

Ala Lys Glu Ser Gly Pro Thr Thr Tyr Lys Val Thr Ser Thr Leu Thr
            180                 185                 190

Ile Lys Glu Ser Asp Trp Leu Gly Gln Ser Met Phe Thr Cys Arg Val
        195                 200                 205

Asp His Arg Gly Leu Thr Phe Gln Gln Gln Ala Ser Ser Met Cys Val
    210                 215                 220

Pro
225

<210> SEQ ID NO 26
<211> LENGTH: 214
<212> TYPE: PRT
<213> ORGANISM: Artificial Sequence
<220> FEATURE:
<223> OTHER INFORMATION: bispecific IgG1 antibody, light chain A

<400> SEQUENCE: 26

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

-continued

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 443
<212> TYPE: PRT
<213> ORGANISM: Artificial Sequence
<220> FEATURE:
<223> OTHER INFORMATION: bispecific IgG1 antibody, heavy chain A

<400> SEQUENCE: 27

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Thr His Thr Cys Pro
    210                 215                 220

```
Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
        260                 265                 270

Asn Trp Tyr Val Asp Gly Val Glu Val His Asn Ala Lys Thr Lys Pro
        275                 280             285

Arg Glu Glu Gln Tyr Asn Ser Thr Tyr Arg Val Val Ser Val Leu Thr
        290             295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Cys Arg
            340                 345                 350

Asp Glu Leu Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn Arg
            420                 425                 430

Phe Thr Gln Lys Ser Leu Ser Leu Ser Pro Gly
            435                 440

<210> SEQ ID NO 28
<211> LENGTH: 220
<212> TYPE: PRT
<213> ORGANISM: Artificial Sequence
<220> FEATURE:
<223> OTHER INFORMATION: bispecific IgG1 antibody, light chain B

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Arg
            100                 105                 110

Thr Val Ala Ser Arg Asp Phe Thr Pro Pro Thr Val Lys Ile Leu Gln
        115                 120                 125

Ser Ser Cys Asp Gly Gly Gly His Phe Pro Pro Thr Ile Gln Leu Leu
    130                 135                 140
```

```
Cys Leu Val Ser Gly Tyr Thr Pro Gly Thr Ile Gln Ile Thr Trp Leu
145                 150                 155                 160

Glu Asp Gly Gln Val Met Asp Val Asp Leu Ser Thr Ala Ser Thr Thr
            165                 170                 175

Gln Glu Gly Glu Leu Ala Ser Thr Gln Ser Glu Leu Thr Leu Ser Gln
        180                 185                 190

Lys His Trp Leu Ser Asp Arg Thr Tyr Thr Cys Gln Val Thr Tyr Gln
    195                 200                 205

Gly His Thr Phe Glu Asp Ser Thr Lys Lys Cys Ala
    210                 215                 220
```

<210> SEQ ID NO 29
<211> LENGTH: 463
<212> TYPE: PRT
<213> ORGANISM: Artificial Sequence
<220> FEATURE:
<223> OTHER INFORMATION: bispecific IgG1 antibody, heavy chain B

<400> SEQUENCE: 29

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Gly Ser Gly Ser Gly Ser Val Ala Ser Arg
        115                 120                 125

Asp Phe Thr Pro Pro Thr Val Lys Ile Leu Gln Ser Ser Cys Asp Gly
    130                 135                 140

Gly Gly His Phe Pro Pro Thr Ile Gln Leu Leu Cys Leu Val Ser Gly
145                 150                 155                 160

Tyr Thr Pro Gly Thr Ile Gln Ile Thr Trp Leu Glu Asp Gly Gln Val
            165                 170                 175

Met Asp Val Asp Leu Ser Thr Ala Ser Thr Thr Gln Glu Gly Glu Leu
        180                 185                 190

Ala Ser Thr Gln Ser Glu Leu Thr Leu Ser Gln Lys His Trp Leu Ser
    195                 200                 205

Asp Arg Thr Tyr Thr Cys Gln Val Thr Tyr Gln Gly His Thr Phe Glu
    210                 215                 220

Asp Ser Thr Lys Lys Cys Ala Gly Ser Gly Ser Gly Ser Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285
```

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Ser Cys
            370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly
            450                 455                 460

<210> SEQ ID NO 30
<211> LENGTH: 225
<212> TYPE: PRT
<213> ORGANISM: Artificial Sequence
<220> FEATURE:
<223> OTHER INFORMATION: Trispecific antibody, light chain A

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
            85                  90                  95

Glu Asp Ser Arg Thr Phe Gly Gly Gly Thr Lys Leu Glu Ile Lys Arg
            100                 105                 110

Thr Val Ile Ala Glu Leu Pro Pro Lys Val Ser Val Phe Val Pro Pro
            115                 120                 125

Arg Asp Gly Phe Phe Gly Asn Pro Arg Lys Ser Lys Leu Ile Cys Gln
            130                 135                 140

Ala Thr Gly Phe Ser Pro Arg Gln Ile Gln Val Ser Trp Leu Arg Glu
145                 150                 155                 160

Gly Lys Gln Val Gly Ser Gly Val Thr Thr Asp Gln Val Gln Ala Glu
            165                 170                 175

Ala Lys Glu Ser Gly Pro Thr Thr Tyr Lys Val Thr Ser Thr Leu Thr
            180                 185                 190

```
Ile Lys Glu Ser Asp Trp Leu Gly Gln Ser Met Phe Thr Cys Arg Val
    195                 200                 205

Asp His Arg Gly Leu Thr Phe Gln Gln Gln Ala Ser Ser Met Cys Val
    210                 215                 220

Pro
225

<210> SEQ ID NO 31
<211> LENGTH: 463
<212> TYPE: PRT
<213> ORGANISM: Artificial Sequence
<220> FEATURE:
<223> OTHER INFORMATION: Trispecific antibody, heavy chain A

<400> SEQUENCE: 31

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Ala Ser Thr Lys Gly Pro Val Ile Ala Glu
        115                 120                 125

Leu Pro Pro Lys Val Ser Val Phe Val Pro Pro Arg Asp Gly Phe Phe
    130                 135                 140

Gly Asn Pro Arg Lys Ser Lys Leu Ile Cys Gln Ala Thr Gly Phe Ser
145                 150                 155                 160

Pro Arg Gln Ile Gln Val Ser Trp Leu Arg Glu Gly Lys Gln Val Gly
                165                 170                 175

Ser Gly Val Thr Thr Asp Gln Val Gln Ala Glu Ala Lys Glu Ser Gly
            180                 185                 190

Pro Thr Thr Tyr Lys Val Thr Ser Thr Leu Thr Ile Lys Glu Ser Asp
        195                 200                 205

Trp Leu Gly Gln Ser Met Phe Thr Cys Arg Val Asp His Arg Gly Leu
    210                 215                 220

Thr Phe Gln Gln Gln Ala Ser Ser Met Cys Val Pro Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320
```

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn Arg Phe Thr Gln Lys Ser Leu Ser Leu Ser Pro Gly Lys
            450                 455                 460

<210> SEQ ID NO 32
<211> LENGTH: 340
<212> TYPE: PRT
<213> ORGANISM: Artificial Sequence
<220> FEATURE:
<223> OTHER INFORMATION: Trispecific antibody, light chain B

<400> SEQUENCE: 32

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
            85                  90                  95

Thr Phe Gly Gly Gly Thr Lys Leu Glu Ile Lys Gly Ser Gly Ser
            100                 105                 110

Ser Gly Ser Gly Gly Asp Ile Gln Met Thr Gln Ser Pro Ser Ser Leu
            115                 120                 125

Ser Ala Ser Val Gly Asp Arg Val Thr Ile Thr Cys Arg Ala Ser Gln
            130                 135                 140

Gly Ile Arg Asn Tyr Leu Ala Trp Tyr Gln Gln Lys Pro Gly Lys Ala
145                 150                 155                 160

Pro Lys Leu Leu Ile Tyr Ala Ala Ser Thr Leu Gln Ser Gly Val Pro
            165                 170                 175

Ser Arg Phe Ser Gly Ser Gly Ser Gly Thr Asp Phe Thr Leu Thr Ile
            180                 185                 190

Ser Ser Leu Gln Pro Glu Asp Val Ala Thr Tyr Tyr Cys Gln Arg Tyr
            195                 200                 205

Asn Arg Ala Pro Tyr Thr Phe Gly Gln Gly Thr Lys Val Glu Ile Lys
            210                 215                 220

```
Gly Gly Ser Gly Ser Ser Gly Ser Gly Gly Gln Pro Lys Ala Ala
225                 230                 235                 240

Pro Ser Val Thr Leu Phe Pro Pro Ser Ser Glu Glu Leu Gln Ala Asn
            245                 250                 255

Lys Ala Thr Leu Val Cys Leu Ile Ser Asp Phe Tyr Pro Gly Ala Val
            260                 265                 270

Thr Val Ala Trp Lys Ala Asp Ser Ser Pro Val Lys Ala Gly Val Glu
            275                 280                 285

Thr Thr Thr Pro Ser Lys Gln Ser Asn Asn Lys Tyr Ala Ala Ser Ser
            290                 295                 300

Tyr Leu Ser Leu Thr Pro Glu Gln Trp Lys Ser His Arg Ser Tyr Ser
305                 310                 315                 320

Cys Gln Val Thr His Glu Gly Ser Thr Val Glu Lys Thr Val Ala Pro
                325                 330                 335

Thr Glu Cys Ser
            340

<210> SEQ ID NO 33
<211> LENGTH: 573
<212> TYPE: PRT
<213> ORGANISM: Artificial Sequence
<220> FEATURE:
<223> OTHER INFORMATION: Trispecific antibody, heavy chain B

<400> SEQUENCE: 33

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gln Val Gln Leu Gln Gln Ser
            115                 120                 125

Gly Pro Glu Leu Val Lys Pro Gly Ala Ser Val Lys Ile Ser Cys Lys
        130                 135                 140

Ala Ser Gly Tyr Ser Phe Thr Ser Tyr Trp Ile His Trp Ile Lys Gln
145                 150                 155                 160

Arg Pro Gly Gln Gly Leu Glu Trp Ile Gly Met Ile Asp Pro Ser Asp
                165                 170                 175

Gly Glu Thr Arg Leu Asn Gln Arg Phe Gln Gly Arg Ala Thr Leu Thr
            180                 185                 190

Val Asp Glu Ser Thr Ser Thr Ala Tyr Met Gln Leu Arg Ser Pro Thr
        195                 200                 205

Ser Glu Asp Ser Ala Val Tyr Tyr Cys Thr Arg Leu Lys Glu Tyr Gly
    210                 215                 220

Asn Tyr Asp Ser Phe Tyr Phe Asp Val Trp Gly Ala Gly Thr Leu Val
225                 230                 235                 240
```

-continued

```
Thr Val Ser Ser Ala Ser Thr Lys Gly Pro Ser Val Phe Pro Leu Ala
            245                 250                 255
Pro Ser Ser Lys Ser Thr Ser Gly Gly Thr Ala Ala Leu Gly Cys Leu
            260                 265                 270
Val Lys Asp Tyr Phe Pro Glu Pro Val Thr Val Ser Trp Asn Ser Gly
            275                 280                 285
Ala Leu Thr Ser Gly Val His Thr Phe Pro Ala Val Leu Gln Ser Ser
            290                 295                 300
Gly Leu Tyr Ser Leu Ser Ser Val Val Thr Val Pro Ser Ser Ser Leu
305                 310                 315                 320
Gly Thr Gln Thr Tyr Ile Cys Asn Val Asn His Lys Pro Ser Asn Thr
                    325                 330                 335
Lys Val Asp Lys Lys Val Glu Pro Lys Ser Cys Asp Lys Thr His Thr
                    340                 345                 350
Cys Pro Pro Cys Pro Ala Pro Glu Leu Leu Gly Gly Pro Ser Val Phe
            355                 360                 365
Leu Phe Pro Pro Lys Pro Lys Asp Thr Leu Met Ile Ser Arg Thr Pro
370                 375                 380
Glu Val Thr Cys Val Val Val Asp Val Ser His Glu Asp Pro Glu Val
385                 390                 395                 400
Lys Phe Asn Trp Tyr Val Asp Gly Val Glu Val His Asn Ala Lys Thr
                    405                 410                 415
Lys Pro Arg Glu Glu Gln Tyr Asn Ser Thr Tyr Arg Val Val Ser Val
                    420                 425                 430
Leu Thr Val Leu His Gln Asp Trp Leu Asn Gly Lys Glu Tyr Lys Cys
            435                 440                 445
Lys Val Ser Asn Lys Ala Leu Pro Ala Pro Ile Glu Lys Thr Ile Ser
450                 455                 460
Lys Ala Lys Gly Gln Pro Arg Glu Pro Gln Val Tyr Thr Leu Pro Pro
465                 470                 475                 480
Cys Arg Asp Glu Leu Thr Lys Asn Gln Val Ser Leu Trp Cys Leu Val
                    485                 490                 495
Lys Gly Phe Tyr Pro Ser Asp Ile Ala Val Glu Trp Glu Ser Asn Gly
            500                 505                 510
Gln Pro Glu Asn Asn Tyr Lys Thr Thr Pro Pro Val Leu Asp Ser Asp
            515                 520                 525
Gly Ser Phe Phe Leu Tyr Ser Lys Leu Thr Val Asp Lys Ser Arg Trp
530                 535                 540
Gln Gln Gly Asn Val Phe Ser Cys Ser Val Met His Glu Ala Leu His
545                 550                 555                 560
Asn His Tyr Thr Gln Lys Ser Leu Ser Leu Ser Pro Gly
                    565                 570
```